(12) United States Patent
Bateman

(10) Patent No.: US 12,066,444 B2
(45) Date of Patent: Aug. 20, 2024

(54) BLOOD-BASED METHODS FOR DETERMINING Aβ AMYLOIDOSIS

(71) Applicant: Washington University, St. Louis, MO (US)

(72) Inventor: Randall Bateman, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/610,428

(22) PCT Filed: May 1, 2018

(86) PCT No.: PCT/US2018/030518
§ 371 (c)(1),
(2) Date: Nov. 1, 2019

(87) PCT Pub. No.: WO2018/204406
PCT Pub. Date: Nov. 8, 2018

(65) Prior Publication Data
US 2021/0255201 A1    Aug. 19, 2021

Related U.S. Application Data

(60) Provisional application No. 62/532,793, filed on Jul. 14, 2017, provisional application No. 62/515,294, filed on Jun. 5, 2017, provisional application No. 62/492,718, filed on May 1, 2017.

(51) Int. Cl.
*G01N 33/68* (2006.01)

(52) U.S. Cl.
CPC . *G01N 33/6896* (2013.01); *G01N 2333/4709* (2013.01)

(58) Field of Classification Search
CPC .............. G01N 33/6896; G01N 2333/4709
See application file for complete search history.

(56) References Cited

U.S. PATENT DOCUMENTS

| | | |
|---|---|---|
| 2009/0041661 A1 | 2/2009 | Hellerstein |
| 2009/0142766 A1 | 6/2009 | Holtzman et al. |
| 2011/0111511 A1 | 5/2011 | Bateman et al. |
| 2011/0166035 A1 | 7/2011 | Kleinschmidt et al. |
| 2012/0015371 A1 | 1/2012 | West et al. |
| 2013/0115716 A1 | 5/2013 | Bateman et al. |
| 2014/0370619 A1 | 12/2014 | Holtzman et al. |
| 2015/0140672 A1* | 5/2015 | Bateman ............. G01N 33/58 436/86 |
| 2015/0212098 A1 | 7/2015 | Van Eyk et al. |
| 2015/0254421 A1 | 9/2015 | Bateman et al. |
| 2016/0169916 A1 | 6/2016 | Holtzman et al. |
| 2016/0178646 A1 | 6/2016 | Bateman et al. |

FOREIGN PATENT DOCUMENTS

| | | |
|---|---|---|
| WO | 2013096451 A2 | 6/2013 |
| WO | 2018204406 A1 | 11/2018 |
| WO | 2020146652 A1 | 7/2020 |

OTHER PUBLICATIONS

Lewczuk et al., Experimental Neurology, 2010, 223:366-70.*
Bateman, R. et al., "Human amyloid-[beta] synthesis and clearance rates as measured in cerebrospinal fluid in vivo," Nat. Med., Jul. 2006, pp. 856-861, vol. 12, No. 7.
Bateman, R. et al., "A Gamma-Secretase Inhibitor Decreases Amyloid-beta Production in the Central Nervous System," NIH Public Access Author Manuscript, Jul 1. 2010, pp. 1-12; published in final form as: Ann. Neurol., Jul. 2009, pp. 48-54, vol. 66, No. 1.
Beach, T. et al., "Accuracy of the Clinical Diagnosis of Alzheimer Disease at National Institute on Aging Alzheimer Disease Centers, 2005-2010," J. Neuropathol. Exp. Neurol., Apr. 2012, pp. 266-273, vol. 71, No. 4.
Bibl, M. et al., "CSF amyloid-beta-peptides in Alzheimer's disease, dementia with Lewy bodies and Parkinson's disease dementia," Brain, May 2006, pp. 1177-1187, vol. 129, Part 5.
Bolus (medicine), definition from Wikipedia, retrieved from internet on Jan. 28, 2016, 2 pgs.
Clark, C. et al., "Cerebrospinal Fluid Tau and beta-Amyloid. How Well Do These Biomarkers Reflect Autopsy-Confirmed Dementia Diagnoses?," Arch Neurol. 2003, pp. 1696-1702, vol. 60.
Cohen, A. et al., "Early detection of Alzheimer's disease using PiB and FDG PET," Neurobiol. Dis., Dec. 2014, pp. 117-122, vol. 72.
Communication Under Rule 71(3) EPC, Intention to Grant, dated Apr. 19, 2017, from related European Patent Application No. 12859548.5; 133 pgs.
Communication Under Rule 71(3) EPC, Intention to Grant, dated Apr. 24, 2017, from related European Patent Application No. 16158001.4; 70 pgs.
Communication Under Rule 71(3) EPC, Intention to Grant, dated Nov. 2, 2015, from related European Patent Application No. 11787251. 5, 35 pgs.
Deane, R. et al., "LRP/Amyloid beta-Peptide Interaction Mediates Differential Brain Efflux of Abeta Isoforms," Neuron, Aug. 5, 2004, pp. 333-344, vol. 43.
Deane, R. et al., "RAGE mediates amyloid-beta peptide transport across the blood-brain barrier and accumulation in brain," Nat. Med., Jul. 2003, pp. 907-913, vol. 9, No. 7.
Examiner's Answer dated Jan. 26, 2018 from related U.S. Appl. No. 13/699,497; 14 pgs.
Extended European Search Report dated Jan. 20, 2016 from related European Patent Application No. 12859548.5; 11 pgs.
Extended European Search Report dated Jul. 20, 2016 from related European Patent Application No. 16158001.4; 6 pgs.
Extended European Search Report dated Nov. 4, 2013 from related European Patent Application No. 11787251.5; 6 ogs.

(Continued)

*Primary Examiner* — Olga N Chernyshev
(74) *Attorney, Agent, or Firm* — Polsinelli PC

(57) ABSTRACT

The present disclosure provides methods for blood-based examination useful to identify subjects with Aβ amyloidosis and/or to identify subjects who should or should not undergo further testing or treatment for Aβ amyloidosis, as well as methods for treating subjects diagnosed with Aβ amyloidosis by the methods disclosed herein.

8 Claims, 12 Drawing Sheets

(56) References Cited

OTHER PUBLICATIONS

Fagan, A. et al., "Inverse Relation between In Vivo Amyloid Imaging Load and Cerebrospinal Fluid A[beta]42 in Humans," Ann. Neurol., 2006, pp. 512-519, vol. 59.
Fukumoto, H. et al., "Age but Not Diagnosis Is the Main Predictor of Plasma Amyloid beta-Protein Levels," Arch Neurol., 2003, pp. 958-964, vol. 60.
Fukuyama, R. et al., "Age-Dependent Change in the Levels of AlphaBeta40 and AlphaBeta42 in Cerebrospinal Fluid from Control Subjects, and a Decrease in the Ratio of AlphaBeta42 to AlphaBeta40 Level in Cerebrospinal Fluid from Alzheimer's Disease Patients," Eur. Neurol., Jan. 1, 2000, pp. 155-160, vol. 43, No. 3.
Galasko, D. et al., "High Cerebrospinal Fluid Tau and Low Amyloid beta42 Levels in the Clinical Diagnosis of Alzheimer Disease and Relation to Apolipoprotein E Genotype," Arch Neurol., 1998, pp. 937-945, vol. 55.
Giedraitis, V. et al., "The normal equilibrium between CSF and plasma amyloid beta levels is disrupted in Alzheimer's disease," Neuroscience Letters, Oct. 29, 2007, pp. 127-131, vol. 427, No. 3.
Graff-Radford, N. et al., "Association of Low Plasma Abeta42/Abeta40 Ratios With Increased Imminent Risk for Mild Cognitive Impairment and Alzheimer Disease," Arch. Neurol., Mar. 2007, pp. 354-362, vol. 64, No. 3.
Hansson, O. et al., "Prediction of Alzheimer's Disease Using the CSF AlphaBeta42/AlphaBeta40 Ratio in Patients with Mild Cognitive Impairment," Dement. Geriatr. Cogn. Disord., Jan. 1, 2007, pp. 316-320, vol. 23, No. 5.
International Search Report and Written Opinion dated Feb. 22, 2013 from related International Patent Application No. PCT/US2012/070623; 9 pgs.
International Search Report and Written Opinion dated Jun. 27, 2018 from related International Patent Application No. PCT/US2018/030518; 12 pgs.
International Search Report and Written Opinion dated Nov. 23, 2011 from related International Patent Application No. PCT/US2011/037754; 8 pgs.
International Search Report and Written Opinion dated Apr. 24, 2020 from related International Patent Application No. PCT/US2020/012959; 13 pgs.
Johnson, K. et al., "Update on Appropriate Use Criteria for Amyloid PET Imaging: Dementia Experts , Mild Cognitive Impairment, and Education," J. Nucl. Med., Jul. 2013, pp. 1011-1013, vol. 54, No. 7.
Kfoury, N. et al., "Trans-cellular Propagation of Tau Aggregation by Fibrillar Species," J. Bio. Chem., Jun. 1, 2012, pp. 19440-19451, vol. 287, No. 23.
Klunk, W. et al., "Imaging Brain Amyloid in Alzheimer's Disease with Pittsburgh Compound-B," Ann. Neurol., 2004, pp. 306-319, vol. 55, No. 3.
Korolev, I. et al., "Predicting Progression from Mild Cognitive Impairment to Alzheimer's Dementia Using Clinical, MRI, and Plasma Biomarkers via Probabilistic Pattern Classification," PLoS One, Feb. 2016, pp. 1-25, vol. 11, No. 2, e0138866.
Lame, M. et al., "Quantification of amyloid beta peptides AlphaBeta1-38, AlphaBeta1-40, and AlphaBeta1-42 in human cerebrospinal fluid by ultra-performance liquid chromatography-tandem mass spectrometry," Anal. Biochem., 2011, pp. 133-139, vol. 419, No. 2.
Lee, N-C. et al., "Blood Beta-Amyloid and Tau in Down Syndrome: A Comparison With Alzheimer's Disease," Frontiers in Aging Neurosci., Jan. 2017, pp. 1-8, vol. 8, No. 316.
Mawuenyega, K. et al., "Amyloid-beta isoform metabolism quantitation by stable isotope-labeled kinetics," Anal. Biochem., Sep. 2013, pp. 56-62, vol. 440.
Mawuenyega, K. et al., "Decreased Clearance of CNS beta-Amyloid in Alzheimer's Disease," Sci., Dec. 24, 2010, p. 1774, vol. 330, No. 6012, with Supporting Online Material, 8 pgs., and NIH Public Access Author Manuscript, 4 pgs.
Mayeux, R. et al., "Plasma A[beta]40 and A[beta]42 and Alzheimer's disease. Relation to age, mortality, and risk," Neurology, Nov. 2003, pp. 1185-1190, vol. 61.
Mayeux, R. et al., "Blood-based biomarkers for Alzheimer's disease: plasma A[beta]40 and A[beta]42, and genetic variants," Neurobiol. Aging, Dec. 2011, pp. S10-S19, vol. 32.
Notice of Acceptance dated Apr. 4, 2018 from related Australian Patent Application No. 2017200029; 3 pgs.
Notice of Acceptance dated Dec. 10, 2014 from related Australian Patent Application No. 2011258462; 4 pgs.
Notice of Allowance dated Jan. 25, 2018 from related Canadian Patent Application No. 2,800,680; 1 pg.
Notice of Decision from Post-Prosecution Pilot Program Conference dated Nov. 8, 2016 from related U.S. Appl. No. 13/699,497; 4 pgs.
Office Action dated Apr. 12, 2017 from related Canadian Patent Application No. 2,800,680; 4 pgs.
Office Action dated Aug. 12, 2014 from related U.S. Appl. No. 13/699,497; 13 pgs.
Office Action dated Aug. 19, 2014 from related Japanese Patent Application No. 2013-512165; 6 pgs., including English translation.
Office Action dated Aug. 24, 2015 from related U.S. Appl. No. 14/366,831; 23 pgs.
Office Action dated Aug. 4, 2016 from related U.S. Appl. No. 13/699,497; 10 pgs.
Office Action dated Aug. 8, 2017 from related Japanese Patent Application No. 2016-023884; 5 pgs., including English translation.
Office Action dated Dec. 16, 2016 from related Australian Patent Application No. 2012359020; 3 pgs.
Office Action dated Dec. 30, 2013 from related U.S. Appl. No. 13/699,497; 15 pgs.
Office Action dated Feb. 6, 2015 from related European Patent Application No. 11787251.5; 5 pgs.
Office Action dated Feb. 8, 2016 from related U.S. Appl. No. 13/699,497; 15 pgs.
Office Action dated Jan. 16, 2015 from related U.S. Appl. No. 14/366,831; 18 pgs.
Office Action dated Jan. 28, 2016 from related Australian Patent Application No. 2015201714; 5 pgs.
Office Action dated Jul. 12, 2016 from related Japanese Patent Application No. 2014-548837; 9 pgs., including English translation.
Office Action dated Jul. 13, 2017 from related U.S. Appl. No. 15/057,694; 15 pgs.
Office Action dated Jul. 16, 2014 from related Australian Patent Application No. 2011258462; 4 pgs.
Office Action dated Jun. 23, 2015 from related Japanese Patent Application No. 2013-512165; 3 pgs., including English translation.
Office Action dated Mar. 10, 2017 from related U.S. Appl. No. 13/699,497; 16 pgs.
Office Action dated Mar. 9, 2017 from related U.S. Appl. No. 15/422,165; 9 pgs.
Office Action dated May 25, 2017 from related Australian Patent Application No. 2017200029; 2 pgs.
Office Action dated Nov. 22, 2016 from related Japanese Patent Application No. 2016-023884; 6 pgs., including English translation.
Office Action dated Nov. 30, 2018 from related Indian Patent Application No. 4816/CHEN/2014; 5 pgs.
Ovod, V. et al., "Amyloid beta concentrations and stable isotope labeling kinetics in human plasma specific to central nervous system amyloidosis," Alzheimer's & Dementia, Jul. 2017, pp. 841-849, vol. 13, No. 8.
Patterson, B. et al., "Age and Amyloid Effects on Human CNS Amyloid-Beta Kinetics," Ann. Neurol., Sep. 2015, pp. 439-453, vol. 78, No. 3.
Potter, R. et al., "Increased in vivo amyloid-beta42 production, exchange, and irreversible loss in presenilin mutations carriers," NIH Public Access Author Manuscript, Nov. 24, 2013, pp. 1-19; published in final format as: Sci. Transl. Med., Jun. 12, 2013, pp. 1-10, vol. 5, Issue 189, Article No. 189ra77.
Roberts, K. et al., "Amyloid-beta Efflux from the Central Nervous System into the Plasma," Ann. Neurol., 2014, pp. 837-844, vol. 76.
Rosman, K.J.R. et al., "Isotopic Compositions of the Elements 1997," Pure & Appl. Chem., 1998, pp. 217-235, vol. 70, No. 1.
Sanchez, L. et al., "ABeta40 and ABeta42 Amyloid Fibrils Exhibit Distinct Molecular Recycling Properties," J. Am. Chem. Soc., Apr. 12, 2011, pp. 6505-6508, vol. 133, No. 17.

(56) References Cited

OTHER PUBLICATIONS

Selkoe, D. et al., "The amyloid hypothesis of Alzheimer's disease at 25 years," EMBO Mol. Med., 2016, pp. 595-608, vol. 8, No. 6.
Shoji, M., "Cerebrospinal Fluid ABeta40 and ABeta42: Natural Course and Clinical Usefulness," Front. Biosci., Apr. 1. 2002, pp. d997-1006, vol. 7.
Sobow, T. et al., "Plasma levels of A[beta]peptides are altered in amnestic mild cognitive impairment but not in sporadic Alzheimer's disease," Acta Neurobiol. Exp., 2005, pp. 117-124, vol. 65.
Yaffe, K. et al., "Association of Plasma beta-Amyloid Level and Cognitive Reserve With Subsequent Cognitive Decline," JAMA, Jan. 19, 2011, pp. 261-266, vol. 305, No. 3.
Hung, Drug Candidates in clinical trails for Alzheimer's disease, Journal of Biomedical Science, 2017, vol. 24, No. 47, 12 pp.
Briggs, Drug treatments in Alzheimer's disease, Clinical Medicine, 2016, vol. 16, No. 3, pp. 247-253.

\* cited by examiner

BLOOD-BASED METHODS FOR DETERMINING Aβ AMYLOIDOSIS

CROSS-REFERENCE TO RELATED APPLICATIONS

This application claims priority to PCT/US2018/30518, filed May 1, 2018, which claims the benefit of U.S. provisional application No. 62/492,718, filed May 1, 2017, U.S. provisional application No. 62/515,294, filed Jun. 5, 2017, and U.S. provisional application No. 62/532,793, filed Jul. 14, 2017, each of which is hereby incorporated by reference in its entirety.

GOVERNMENTAL RIGHTS

This invention was made with government support under NS065667 and AG061900 awarded by the National Institutes of Health. The government has certain rights in the invention.

FIELD OF THE INVENTION

The present invention relates to methods for blood-based examination useful to identify subjects with Aβ amyloidosis and/or to identify subjects who should or should not undergo further testing or treatment for Aβ amyloidosis, as well as methods for treating subjects diagnosed with Aβ amyloidosis by the methods disclosed herein.

BACKGROUND OF THE INVENTION

Aggregation and accumulation of amyloid-beta (AB) in the central nervous system, particularly Aβ42, is implicated in the pathogenesis of several neurodegenerative diseases. Unfortunately, current methods for clinically defined evidence of Aβ deposition have a number of limitations. Neuroimaging studies have emerged as tools for detection of cerebral Aβ amyloidosis; however, their use is limited by expense and availability. Furthermore, dysregulated Aβ kinetics may precede imaging-based amyloid detection by many years. Decreased cerebrospinal fluid (CSF) Aβ42 levels and increased CSF tau are associated with amyloidosis and risk of progression to dementia. However, CSF collection has perceived invasiveness, requires specialty training with relatively few practitioners for screening large numbers, and standardization of CSF biomarkers for clinical use is lacking.

A blood-based marker of Aβ amyloidosis would have many advantages, including cost, speed, and accessibility. However, prior studies attempting to correlate blood Aβ42 levels with central nervous system amyloidosis have not demonstrated highly significant differences.

Accordingly, there remains a need in the art for methods and compositions which allow for accurate and specific measurements of Aβ in blood.

SUMMARY OF THE INVENTION

In an embodiment, the present invention provides a method for detecting Aβ amyloidosis, the method comprising: (a) measuring the concentration of Aβ42 and Aβ40 in a blood sample obtained from the subject, and then calculating the Aβ42/Aβ40 concentration ratio; and (b) identifying the subject as amyloid d positive when the Aβ42/Aβ40 concentration ratio is less than 0.126, and the Aβ42/Aβ40 concentration ratio is obtained by a system that provides a probability of detecting Aβ amyloidosis equal to or greater than about 85%.

In an embodiment, the present invention provides a method for detecting Aβ amyloidosis, the method comprising: (a) measuring the concentration of Aβ42 and Aβ40 in a blood sample obtained from the subject, and then calculating the Aβ42/Aβ40 concentration ratio; and (b) comparing the Aβ42/Aβ40 concentration ratio obtained in step (a) to a predetermined threshold calculated by using a receiver operating characteristic (ROC) curve, and identifying the subject as a candidate further diagnostic testing and/or a therapeutic intervention when the Aβ42/Aβ40 concentration ratio is lower than the predetermined threshold; wherein the predetermined threshold is obtained by a system that provides a probability of detecting Aβ amyloidosis equal to or greater than about 85%.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

FIG. 1 depicts Plasma Aβ SILK for Aβ38, Aβ40, and Aβ42.

FIG. 3 depicts a graph showing that the concentration of Aβ42/Aβ40 remains relatively stable over time with measurable separation of clinical groups.

Figure 1A:
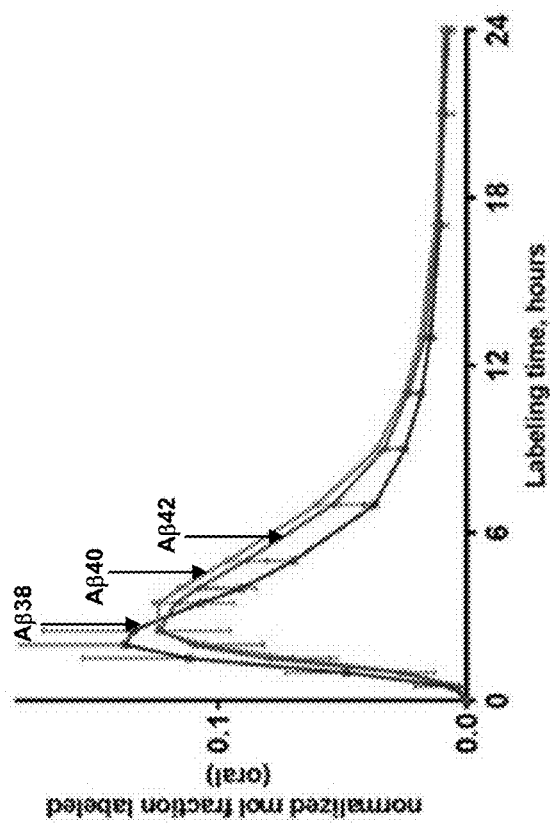
FIG. 1A shows the average isotopic enrichment time course profiles normalized to plasma leucine for plasma Aβ38 (blue), Aβ40 (green), and Aβ42 (red) (mean+/−95% CI) by labeling protocol (left: IV bolus; right: oral). Kinetic profiles of all three isoforms appear similar between labeling protocols, with Aβ38 reaching its labeling peak before Aβ40 and Aβ42.
Figure 1A:
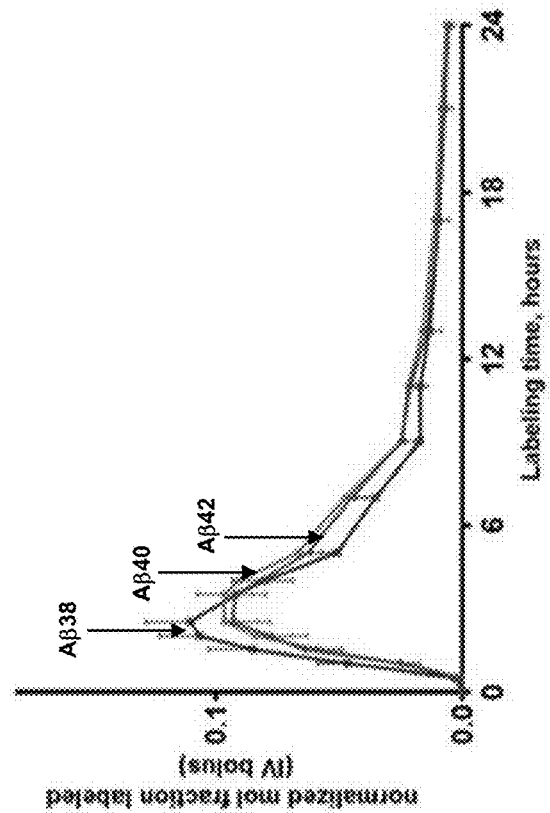

Various embodiments of the present invention will be described in detail with reference to the figures, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present invention relates to blood-based methods for detecting Aβ amyloidosis, and a system therefor. While Aβ42/Aβ40 ratios in the CSF are decreased by about 50% in the presence of Aβ amyloidosis, Aβ42/Aβ40 ratios in blood are decreased on average by 14% in amyloid positive subjects as compared to amyloid negative subjects (see the Examples). Importantly, the methods and systems described herein measure plasma concentrations of individual Aβ species with a high degree of precision. These precise measurements allow the small differences in plasma Aβ42 concentration between amyloid positive and amyloid negative subjects to be quantified accurately and therefore have clinical utility. The systems of the present invention provide a cut-off value that has a sensitivity of about 95% and a specificity of about 70% for amyloid-positive subjects. Alternatively, or in addition, the systems of the present invention have a probability for detecting Aβ amyloidosis equal to or greater than about 80%, more preferably 85%. Accordingly, the present invention also relates to methods to inform and direct clinical decisions including, but not limited to, conducting further diagnostic tests, enrolling a subject in a clinical trial, and initiating or continuing medical treatment. Other objects, advantages and features of the present invention will become apparent from the following description taken in conjunction with the accompanying figures.

The embodiments of this invention are not limited to particular method steps, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation of in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also be ±4%, 3%, 2%, 1%, etc. Whether or not modified by the term "about," the claims include equivalents to the quantities.

The term "Aβ" refers to peptides derived from a region in the carboxy terminus of a larger protein called amyloid precursor protein (APP). The gene encoding APP is located on chromosome 21. There are many forms of Aβ that may have toxic effects: Aβ peptides are typically 37-43 amino acid sequences long, though they can have truncations and modifications changing their overall size. They can be found in soluble and insoluble compartments, in monomeric, oligomeric and aggregated forms, intracellularly or extracellularly, and may be complexed with other proteins or molecules. The adverse or toxic effects of Aβ may be attributable to any or all of the above noted forms, as well as to others not described specifically. For example, two such Aβ isoforms include Aβ40 and Aβ42; with the Aβ42 isoform being particularly fibrillogenic or insoluble and associated with disease states. The term "Aβ" typically refers to a plurality of Aβ species without discrimination among individual Aβ species. Specific Aβ species are identified by the size of the peptide, e.g., Aβ42, Aβ40, Aβ38 etc.

As used herein, the term "Aβ42/Aβ40 value" means the ratio of the concentration of Aβ42 in a blood sample obtained from a subject compared to the concentration of Aβ40 in the same blood sample.

As used herein, the term "Aβ42/Aβ$_{xx}$ value" means the ratio of the concentration of Aβ42 in a blood sample obtained from a subject compared to the concentration of another Aβ species in the same blood sample.

"Aβ amyloidosis" is clinically defined as evidence of Aβ deposition in the brain. A subject that is clinically determined to have Aβ amyloidosis is referred to herein as "amyloid positive," while a subject that is clinically determined to not have Aβ amyloidosis is referred to herein as "amyloid negative." Aβ amyloidosis likely exists before it is detectable by current techniques. Nonetheless, there are accepted indicators of Aβ amyloidosis in the art. At the time of this disclosure, Aβ amyloidosis is typically identified by amyloid imaging (e.g., PiB PET, fluorbetapir, or other imaging methods known in the art) or by decreased cerebrospinal fluid (CSF) Aβ42 or a decreased CSF Aβ42/40 ratio. [$^{11}$C] PIB-PET imaging with mean cortical binding potential (MCBP) score>0.18 is an indicator of Aβ amyloidosis, as is cerebral spinal fluid (CSF) Aβ42 concentration of about 1 ng/ml by immunoprecipitation and mass spectrometry (IP/MS)). Values such as these, or others known in the art, may be used alone or in combination to clinically confirm Aβ amyloidosis. See, for example, Klunk W E et al. *Ann Neurol* 55(3) 2004, Fagan A M et al. *Ann Neurol*, 2006, 59(3), Patterson et. al, *Annals of Neurology*, 2015, 78(3): 439-453, or Johnson et al., *J. Nuc. Med.*, 2013, 54(7): 1011-1013, each hereby incorporated by reference in its entirety. Subjects with Aβ amyloidosis may or may not be symptomatic, and symptomatic subjects may or may not satisfy the clinical criteria for a disease associated with Aβ amyloidosis. Non-limiting examples of symptoms associated with Aβ amyloidosis may include impaired cognitive function, altered behavior, abnormal language function, emotional dysregulation, seizures, dementia, and impaired nervous system structure or function. Diseases associated with Aβ amyloidosis include, but are not limited to, Alzheimer's Disease (AD), cerebral amyloid angiopathy, Lewy body dementia, and inclusion body myositis. Subjects with Aβ amyloidosis are at an increased risk of developing a disease associated with Aβ amyloidosis.

As used herein, the term "Aβ-free antibody" or "substantially Aβ-free antibody" refers to an anti-Aβ antibody completely lacking Aβ contamination or having such a small amount of bound Aβ that the Aβ contamination does not affect the performance of the antibody (e.g. "substantially free from Aβ contamination"). Suitable methods for generating Aβ-free antibody and substantially Aβ-free antibody are known in the art. For example, the antibody preparation that is substantially Aβ-free can be produced by culturing a hybridoma producing the desired anti-Aβ antibody in serum-free medium, and optionally in the presence of a beta-secretase inhibitor and/or a gamma-secretase inhibitor. Methods of culturing and producing hybridomas are well known in the art.

As used herein, the term "probability for detecting Aβ amyloidosis" refers to the extent to which detection is likely to occur, and is an indicator of the accuracy of a diagnostic test.

As used herein, the term "ROC" means "receiver operating characteristic". A ROC analysis may be used to evaluate the diagnostic performance, or predictive ability, of a test or a method of analysis. A ROC graph is a plot of sensitivity and specificity of a test at various thresholds or cut-off values. Each point on a ROC curve represents the sensitivity and its respective specificity. A threshold value can be selected based on an ROC curve to identify a point where sensitivity and specificity both have acceptable values, and this value can be used in applying the test for diagnostic purposes. If specificity only is optimized, then the test will be less likely to generate a false positive (diagnosis of the disease in more subjects who do not have the disease) at the cost of an increased likelihood that some cases of disease will not be identified (e.g. false negatives). If sensitivity is only optimized, the test will be more likely to identify most or all of the subjects with the disease, but will also diagnose the disease in more subjects who do not have the disease (e.g. false positives). A user is able to modify the parameters, and therefore select an ROC threshold value suitable for a given clinical situation, in ways that will be readily understood by those skilled in the art.

Another useful feature of the ROC curve is an area under the curve (AUC) value, which quantifies the overall ability of the test to discriminate between different sample properties, in this case to discriminate between those subjects with Aβ amyloidosis (i.e. amyloid positive) and those without Aβ amyloidosis (i.e. amyloid negative). A test that is no better at identifying true positives than random chance will generate a ROC curve with an AUC of 0.5. A test having perfect specificity and sensitivity (i.e., generating no false positives and no false negatives) will have an AUC of 1.00. In reality, most tests will have an AUC somewhere between these two values.

As used herein, the term "sensitivity" refers to the percentage of truly positive observations which is classified as such by a test, and indicates the proportion of subjects correctly identified as amyloid positive. In other words, sensitivity is equal to (true positive result)/[(true positive result)+(false negative result)].

As used herein, the term "specificity" refers to the percentage of truly negative observations which is classified as such by a test, and indicates the proportion of subjects correctly identified as amyloid negative. In other words, the percentage of healthy people who are correctly identified as not having a condition. Specificity is equal to (true negative result)/[(true negative result)+(false positive result).

In one embodiment, the range of the highest sensitivity is from 0.8 to 1. In another embodiment, the range of the highest specificity is from 0.8 to 1. In one embodiment, the range of the highest sensitivity is from 0.8 to 1 and the range of the highest specificity is from 0.8 to 1.

As used herein, the term "subject" refers to a mammal, preferably a human. The mammals include, but are not limited to, humans, primates, livestock, rodents, and pets. A subject may be waiting for medical care or treatment, may be under medical care or treatment, or may have received medical care or treatment.

As used herein, the term "healthy control group," "normal group" or a sample from a "healthy" subject means a subject, or group subjects, who is/are diagnosed by a physician as not suffering from Aβ amyloidosis, or a clinical disease associated with Aβ amyloidosis (including but not limited to Alzheimer's disease) based on qualitative or quantitative test results. A "normal" subject is usually about the same age as the individual to be evaluated, including, but not limited, subjects of the same age and subjects within a range of 5 to 10 years.

As used herein, the term "blood sample" refers to a biological sample derived from blood, preferably peripheral (or circulating) blood. The blood sample can be whole blood, plasma or serum, although plasma is typically preferred.

The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

II. Method for Detecting Ab Amyloidosis

One aspect of the present invention is a blood-based method for detecting Aβ amyloidosis. Generally speaking, the method comprises detecting and quantifying the concentration of Aβ42, and optionally one other Aβ peptide, in a blood sample obtained from a subject, and comparing the Aβ42 concentration (or the Aβ42/Aβ$_{xx}$ value) to a predetermined threshold value. Importantly, the methods described herein measure plasma concentrations of individual Aβ species with a high degree of precision. These precise measurements allow the small differences in plasma Aβ42 concentration between amyloid positive and amyloid negative subjects to be quantified accurately. As a result, the method can be used to produce a system that has a probability for detecting Aβ amyloidosis equal to or greater than about 80%, more preferably 85%. Alternatively, or in addition, the system can be used to establish to a cut-off value for amyloid-positive subjects that has a sensitivity of about 80% or higher and a specificity of about 70% or higher.

The method is not limited to a particular group of subjects. For example, the method may be incorporated into routine screening practices performed by general medical practitioners or specialists. In various other embodiments, a subject may be a participant in a clinical trial, a subject at risk of developing Aβ amyloidosis (e.g., due to known genetic, environmental, or lifestyle risks), a subject with at least one symptom of Aβ amyloidosis, or a subject initiating or continuing treatment for Aβ amyloidosis or a clinical disease associated with Aβ amyloidosis.

In embodiments that measure the concentration of Aβ42 and at least one other Aβ peptide (Aβ$_{xx}$), the other Aβ peptide may be Aβ40, Aβ38, or any other Aβ peptide. In preferred embodiments, the other Aβ peptide is Aβ40 or Aβ38.

(a) Blood Sample

A blood sample obtained from a subject is required. A blood sample may contain Aβ that is not modified to include a detectable label ("unlabeled Aβ"), or the sample may contain in vivo labeled Aβ. The term "in vivo labeled Aβ" refers to Aβ that was labeled in vivo following administration of label to a subject. Suitable labels are known in the art and include, but are not limited to, amino acids or amino acid precursors labeled with radioactive or non-radioactive isotopes. See, for example, US 20090142766 and US 20130115716, each hereby incorporated by reference in its entirety. Although in vivo labeling methods may increase the sensitivity of a detection method, an advantage of the present invention is that in vivo labeled Aβ is not required. In a preferred embodiment, the blood sample contains unlabeled Aβ. In another preferred embodiment, the blood sample does not contain in vivo labeled Aβ.

The blood sample should typically be large enough to allow the measurement of Aβ. A typical blood sample may be from about 0.5 ml to about 10 ml. More than one sample may be pooled for a particular time point. The blood sample may be collected directly as part of the method. Alternatively, a previously-obtained blood sample may be used. Methods of collecting a blood sample are well known in the art. For example, venipuncture, with or without a catheter, may be used to collect a blood sample. In another example, a finger stick, or the equivalent, may be used to collect a blood sample. Additives may or may not be added to the collected blood prior to plasma separation. Suitable additives include citrate, heparin, EDTA, Tween, and protease inhibitors.

(b) Detecting and Quantifying Aβ Peptides

The method of detecting and quantifying Aβ in a blood sample can and will vary but should be sensitive and precise enough to accurately quantify the concentration of Aβ in blood. A non-limiting measurement of assay precision is the coefficient of variation (CV). In some embodiments, the CV may be less than 5%. In some embodiments, the CV may be about 2-3%. [Expand] Suitable methods are known in the art and include, but are not limited to, capture-specific assays, in particular antibody-based assays (e.g. ELISA, xMAP® technology, single molecule array (SIMOA™) technology, etc.), and high resolution mass spectrometry. Generally speaking, the method of detecting Aβ may also be used to quantify the concentration of Aβ. In some embodiments, quantification encompasses determining the Aβ42/Aβ$_{xx}$ value.

A blood sample, typically in the form of a plasma sample, may be used directly. Generally, however, additional processing of the sample occurs prior to analyzing the sample. In a preferred embodiment, one or more protease inhibitors are added to the sample. There are numerous commercial sources for protease inhibitors and protease inhibitor cocktails. In various other embodiments, additional techniques may be used to separate Aβ from other blood components (either partially or completely), or to concentrate the Aβ in a sample. As an example, immunoprecipitation may be used to partially or completely purify Aβ before it is analyzed. The immunoprecipitation antibody may be attached to a solid support, such as a bead or resin. Use of an antibody that binds to the mid-domain of Aβ can be used to immunoprecipitate multiple Aβ peptides, while selection of an antibody that binds to the N- or C-terminus of Aβ can be used to immunoprecipitate a subset of Aβ peptide(s). Protocols for immunoprecipitations are known in the art. Other methods of separating or concentrating Aβ may be used alone or in combination with immunoprecipitation. For example, chromatography techniques may be used to separate Aβ (or fragments thereof) by size, hydrophobicity or affinity. Aβ may also be cleaved into smaller peptides prior to detection. For instance, Aβ may be enzymatically cleaved with a protease to create several small peptides. Suitable proteases include, but are not limited to, trypsin, Lys-N, Lys-C, and Arg-N.

In one embodiment, a capture-specific assay is used. Prior to analyzing the sample, one or more protease inhibitors are added to the sample. The sample, now containing one or more protease inhibitor(s), is then analyzed to determine the concentration of Aβ42. In certain embodiments, the concentration of at least one other Aβ peptide is also determined, for example Aβ40 and/or Aβ38. In a preferred embodiment, the capture-specific reagent of the assay is an antibody that is substantially Aβ-free.

In another embodiment, high-resolution tandem mass spectrometry is used. Prior to analyzing the sample, one or more protease inhibitors are added to the sample and then Aβ is immunoprecipitated using an anti-Aβ antibody, preferably an anti-Aβ antibody that specifically binds all targeted Aβ peptides. In a preferred embodiment, the immunoprecipitation antibody is an antibody that is substantially Aβ-free. Following one or more wash steps, the bound Aβ peptides are proteolytically digested. Suitable proteases include, but are not limited to, trypsin, Lys-N, Lys-C, and Arg-N. Digestion may occur following elution or while the Aβ peptides are bound to the immunoprecipitation antibody. Following one or more clean-up steps, digested Aβ peptides are analyzed by a liquid chromatography system interfaced with a high-resolution tandem MS unit (LC-MS/MS).

Additional processing of the sample may also occur prior to LC-MS/MS analysis. For example, the sample may be further processed following digestion by trichloroacetic acid (TCA) or trifluoroacetic acid (TFA) precipitation. Due to the high plasma protein to Aβ concentration ratio, and polymer and near-isobaric contamination (e.g., PEG or other buffer components), at the higher retention times that Aβ is detected by LC-MS/MS, accurate measurement of Aβ can be problematic when processing plasma. As a result, PEG and other contaminants cause ion suppression of Aβ peptides in the mass spectrometer. Beneficially, TCA or TFA precipitation can reduce such contamination. Alternatively, or in addition, the sample may be further processed following digestion (and optional TCA/TFA precipitation) with peracids, in non-limiting examples, performic acid (PFA), peracetic acid (PAA), pertrifluoroacetic acid (PTFA) and such other peracids. This results in derivatization of Aβ to make it less hydrophobic and subsequently moving it away from the retention times of many hydrophobic contaminants.

In an exemplary embodiment, the mass spectrometry protocol outlined in the Examples is used.

(c) Comparison to a Predetermined Threshold Value

Detection of Aβ amyloidosis occurs when the Aβ42 concentration (or Aβ42/Aβ$_{xx}$ value) in a blood sample obtained from a subject is lower than a predetermined threshold value that discriminates amyloid positive subjects from amyloid negative subjects, and when the predetermined threshold is obtained by a system that provides a probability of detecting Aβ amyloidosis equal to or greater than 80%, preferably at least about 85%.

As used herein, the term "system" refers to the set of procedures used to determine a threshold value that discriminates amyloid positive subjects from amyloid negative subjects, including but not limited the reagents, the assay used to detect and quantify Aβ, and the statistical methods used in the analysis. In addition, a system has either been validated to perform at a level that has a probability of detecting Aβ amyloidosis equal to or greater than 80%, or the system presently performs at said level even though validation has not been performed.

In one embodiment, the method for detecting and quantifying Aβ is selected from those disclosed in Section II(b), and the predetermined threshold value and probability of detecting Aβ amyloidosis is calculated by using a receiver operating characteristic (ROC) curve or other substantially similar method known in the art. For example, an ROC curve may be generated using the covariates Aβ42 concentration (or Aβ42/Aβxx value) and amyloid status (i.e. amyloid positive or amyloid negative) using blood samples obtained from amyloid positive or amyloid negative individuals of the same species as the subject. A plot is thus generated, which can be used to determine the sensitivity and specificity of various Aβ42 concentrations (or Aβ42/Aβ$_{xx}$ values) for predicting amyloid status. Area under the ROC curve may be used to evaluate the diagnostic accuracy. For example, an ROC AUC of 0.80 indicates there is an 80% probability that a randomly chosen individual with Aβ amyloidosis would have lower plasma Aβ42/Aβ40 value compared to a randomly chosen individual without Aβ amyloidosis. Various methods are known in the art for determining an optimal cut-off value that maximizes sensitivity and specificity to serve as a threshold for discriminating amyloid positive subjects. In one embodiment, the predetermined threshold is determined by a data point of the highest specificity at the highest sensitivity on the ROC curve.

III. Blood-Based Biomarker of Aβ Amyloidosis

Another aspect of the present invention is a blood-based biomarker of Aβ amyloidosis, wherein the blood-based biomarker is an Aβ42/Aβ40 value less than 0.126, determined by a system that provides a probability of detecting Aβ amyloidosis equal to or greater than about 80%, more preferably 85%. Stated another way, an Aβ42/Aβ40 value that can be used to identify an amyloid positive subject is an Aβ42/Aβ40 value less than 0.126.

In some embodiments, a blood-based biomarker of Aβ amyloidosis is an Aβ42/Aβ40 value less than about 0.125, preferably less than about 0.124. Alternatively, an Aβ42/Aβ40 value that can be used to identify an amyloid positive subject may be less than about 0.123, less than about 0.120, or less than about 0.117. In another example, an Aβ42/A340 value that can be used to identify an amyloid positive subject may be less than about 0.115. In an exemplary embodiment, an Aβ42/Aβ40 value that indicates a subject is amyloid positive is an Aβ42/Aβ40 value of about 0.113 or less. In another exemplary embodiment, an Aβ42/Aβ40 value that indicates a subject is amyloid positive is an Aβ42/Aβ40 value of about 0.109 to about 0.113. In each of the above embodiments, the blood-based biomarker of Aβ amyloidosis described above can be optionally combined with an additional biomarker to further improve the diagnostic accuracy.

Another aspect of the present invention is a blood-based biomarker of Aβ amyloidosis, wherein the blood-based biomarker is an Aβ42/Aβ$_{xx}$ value, wherein Aβ$_{xx}$ is an Aβ peptide other than Aβ42. One of skill in the art will be able to determine values for other Aβ peptides based on the disclosures herein.

Methods for detecting and quantifying Aβ peptides are known, and also described in Section II.

IV. Methods for Identifying a Subject as a Candidate for Further Diagnostic Testing and/or Therapeutic Intervention Another aspect of the present invention is a method for identifying or classifying a subject as a candidate for further diagnostic testing and/or for therapeutic intervention. The method comprises detecting and quantifying the concentration of Aβ42 and one other Aβ peptide in a blood sample obtained from a subject, and identifying or classifying the subject as a candidate further diagnostic testing and/or therapeutic intervention when the subject tests positive for a blood-based biomarker of Section III or has a blood Aβ42 concentration (or a ratio of Aβ42 concentration to the concentration of another Aβ peptide) that is less than a predetermined threshold value, as described in Section II.

The method is not limited to a particular group of subjects. For example, the method may be incorporated into routine screening practices performed by general medical practitioners or specialists. In various other embodiments, a subject may be a participant or potential participant in a clinical trial, a subject at risk of developing Aβ amyloidosis (e.g., due to known genetic, environmental, or lifestyle risks), or a subject with at least one symptom of Aβ amyloidosis.

It may be advantageous to use the methods disclosed herein to identify subjects in need of further diagnostic testing because the state-of-the-art test for Aβ amyloidosis, or diseases associated with Aβ amyloidosis, are limited by expense and availability, while the methods disclosed herein are minimally invasive and versatile. In some embodiments, a further diagnostic test is a cerebral spinal fluid (CSF) test to measure the concentration of one or more biomolecules found in the CSF. Non-limiting examples include one or more Aβ peptide, in particular Aβ42, tau, phospho-tau, and ApoE. In other embodiments, a further diagnostic test is a neuroimaging test, such as a structural imaging test, a functional imaging test, or a molecular imaging test. Structural imaging tests are typically performed by magnetic resonance imaging (MRI) and/or computed tomography (CT) to provide information about the shape, position, or volume of brain tissue. Functional imaging tests are typically performed by positron emission testing (PET) and functional MRI (fMRI) to measure cellular activity in one or more regions of the brain. A non-limiting example of a functional imaging test is fluorodeoxyglucose (FDG)-PET. Molecular imaging tests use highly targeted radiotracers to detect cellular or chemical changes and are performed by technologies including PET, fMRI, and single photon emission computed tomography (SPECT). Non-limiting examples of a molecular imaging test include Pittsburgh compound B (PIB)-PET, florbetaben-PET, florbetapir-PET, and flutemetamol-PET.

The methods disclosed herein may also be used to identify subjects in need of therapeutic intervention. In some embodiments, therapeutic intervention may slow, inhibit or reverse amyloid deposition. Until such interventions advance from clinical trial stages, the methods disclosed herein may be used to identify subjects for enrollment in clinical trials and/or evaluate a subject's status during a clinical trial. In embodiments where a subject has one or more symptoms of Aβ amyloidosis, therapeutic intervention may slow or inhibit the worsening of the symptom and/or slow, inhibit, or prevent the onset of new symptoms.

V. Methods for Treating a Subject with Aβ Amyloidosis

Another aspect of the invention is a method for treating a subject with a non-pharmacological treatment, a pharmacological treatment, or an imaging agent based on the subject's positive test result for a blood-based biomarker of Section III or the subject's blood Aβ42 concentration (or a ratio of Aβ42 concentration to the concentration of another Aβ peptide) as described in Section II.

In one embodiment, the method comprises measuring the Aβ42 concentration in a blood sample obtained from a subject, wherein the subject is diagnosed with Aβ amyloidosis when the Aβ42 concentration is less than a predetermined threshold value that discriminates amyloid positive subjects from amyloid negative subjects and the predetermined threshold is obtained by a system that provides a probability of detecting Aβ amyloidosis equal to or greater than 80%, preferably at least about 85%; and administering a treatment to the diagnosed subject. The predetermined threshold value can be set as required by situational circumstances. For example, in certain clinical situations it may be desirable to minimize false-positive rates. These clinical situations may include, but are not limited to, the use of an experimental treatment (e.g., in a clinical trial) or the use of a treatment associated with serious adverse events and/or a higher than average number of side effects. Alternatively, it may be desirable to minimize false-negative rates in other clinical situations. Non-limiting examples may include treatment with a non-pharmacological intervention, the use of a treatment with a good risk-benefit profile, or treatment with a functional imaging agent, a molecular imaging agent (e.g., a radioimaging agent, etc.) followed by detection with PET, fMRI, SPECT, or the like. In certain embodiments, the method further comprises measuring the concentration of another Aβ variant (Aβxx) in the blood sample, wherein the subject is diagnosed with Aβ amyloidosis when the blood Aβ42/Aβxx value is less than a predetermined threshold value that discriminates amyloid positive subjects from amyloid negative subjects. In preferred embodiments, Aβxx is Aβ42, Aβ40, or Aβ38.

In another embodiment, the method comprises requesting a test that provides the results of an analysis determining whether the subject has an Aβ42 blood concentration less than a predetermined threshold value that discriminates amyloid positive subjects from amyloid negative subjects, wherein the Aβ42 blood concentration was obtained by a system that provides a probability of detecting Aβ amyloidosis equal to or greater than 80%, preferably at least about 85%; diagnosing the subject with Aβ amyloidosis when the test results indicate the subject's Aβ42 blood concentration is less than a predetermined threshold value; and administering a treatment to the diagnosed subject. Requesting at test, as used herein, may refer to a physician requesting or ordering a test from a third party, from an in-house laboratory facility, or from a scientific lab capable of performing the test. The predetermined threshold value can be set as required by situational circumstances. For example, in certain clinical situations it may be desirable to minimize false-positive rates. These clinical situations may include, but are not limited to, the use of an experimental treatment (e.g., in a clinical trial) or the use of a treatment associated with serious adverse events and/or a higher than average number of side effects. Alternatively, it may be desirable to minimize false-negative rates in other clinical situations. Non-limiting examples may include treatment with a non-pharmacological intervention, the use of a treatment with a good risk-benefit profile, or treatment with a functional imaging agent, a molecular imaging agent (e.g., a radioimaging agent, etc.) followed by detection with PET, fMRI, SPECT, or the like. Alternatively, it may be desirable to maximize both sensitivity and specificity. In certain embodiments, the method further comprises requesting a test that provides the results of an analysis determining whether the patient has a blood Aβ42/Aβxx value less than a predetermined threshold value that discriminates amyloid positive subjects from amyloid negative subjects; and diagnosing the subject with Aβ amyloidosis when the test results indicated the subject's blood Aβ42/Aβxx value is less than a predetermined threshold value. In preferred embodiments, Aβxx is Aβ42, Aβ40, or Aβ38.

In another embodiment, the method comprises measuring the Aβ42 concentration and the Aβ40 concentration in a blood sample obtained from a subject, wherein the subject is diagnosed with Aβ amyloidosis when the calculated Aβ42/Aβ40 value is less than 0.126, as determined by a system that provides a probability of detecting Aβ amyloidosis equal to or greater than 80%, or optionally equal to or greater than about 85%; and administering a treatment to the diagnosed subject. In further embodiments, the Aβ42/Aβ40 value may be less than about 0.124, less than about 0.123, or less than about 0.120. In still further embodiments, the Aβ42/Aβ40 value may be less than about 0.117 or less than about 0.115. In still further embodiments, the Aβ42/Aβ40 value may be less about 0.113 or less. Alternatively, the Aβ42/Aβ40 value may be about 0.109 to about 0.113. The treatment may be a non-pharmacological treatment, a pharmacological treatment, or treatment with an imaging agent followed by detection of the imaging agent (e.g. with PET, fMRI, SPECT, or the like).

In another embodiment, the method comprises requesting a test that provides the results of an analysis determining whether the subject has an Aβ42/Aβ40 blood value less than 0.126, as determined by a system that provides a probability of detecting Aβ amyloidosis equal to or greater than 80%, or optionally equal to or greater than about 85%; diagnosing the subject with Aβ amyloidosis when the test results indicate the subject's blood Aβ42/Aβ40 value is less than 0.126, and administering a treatment to the diagnosed subject. In further embodiments, the Aβ42/Aβ40 value may be less than about 0.124, less than about 0.123, less than about 0.120, or less than about 0.117. In still further embodiments, the Aβ42/Aβ40 value may be less than about 0.115, or a value of about 0.113 or less. Alternatively, the Aβ42/Aβ40 value may be about 0.109 to about 0.113. The treatment may be a non-pharmacological treatment, a pharmacological treatment, or treatment with an imaging agent followed by detection with PET, fMRI, SPECT, or the like.

Non-limiting examples of non-pharmacological treatments include cognitive behavioral therapy, psychotherapy, behavioral management therapy, Montessori activities, memory training, massage, aromatherapy, music therapy, dance therapy, animal assisted therapy, and multi-sensory therapy. Non-limiting examples of pharmacological treatments include cholinesterase inhibitors, N-methyl D-aspartate (NMDA) antagonists, antidepressants (e.g., selective serotonin reuptake inhibitors, atypical antidepressants, aminoketones, selective serotonin and norepinephrine reuptake inhibitors, tricyclic antidepressants, etc.), gamma-secretase inhibitors, beta-secretase inhibitors, anti-Aβ antibodies (including antigen-binding fragments, variants, or derivatives thereof), anti-tau antibodies (including antigen-binding fragments, variants, or derivatives thereof), stem cells, dietary supplements (e.g. lithium water, omega-3 fatty acids with lipoic acid, long chain triglycerides, genistein, resveratrol, curcumin, and grape seed extract, etc.), antagonists of the serotonin receptor 6, p38alpha MAPK inhibitors, recombinant granulocyte macrophage colony-stimulating factor, passive immunotherapies, active vaccines (e.g. CAD106, AF20513, etc.), tau protein aggregation inhibitors (e.g. TRx0237, methylthionimium chloride, etc.), therapies to improve blood sugar control (e.g., insulin, exenatide, liraglutide pioglitazone, etc.), anti-inflammatory agents, phosphodiesterase 9A inhibitors, sigma-1 receptor agonists, kinase inhibitors, angiotensin receptor blockers, CB1 and/or CB2 endocannabinoid receptor partial agonists, β-2 adrenergic receptor agonists, nicotinic acetylcholine receptor agonists, 5-HT2A inverse agonists, alpha-2c adrenergic receptor antagonists, 5-HT 1A and 1D receptor agonists, Glutaminyl-peptide cyclotransferase inhibitors, selective inhibitors of APP production, monoamine oxidase B inhibitors, glutamate receptor antagonists, AMPA receptor agonists, nerve growth factor stimulants, HMG-CoA reductase inhibitors, neurotrophic agents, muscarinic M1 receptor agonists, GABA receptor modulators, PPAR-gamma agonists, microtubule protein modulators, calcium channel blockers, antihypertensive agents, statins, and any combination thereof.

Non-limiting examples of imaging agents include functional imaging agents (e.g. fluorodeoxyglucose, etc.) and molecular imaging agents (e.g., Pittsburgh compound B, florbetaben, florbetapir, flutemetamol, radionuclide-labeled antibodies, etc.)

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Forty-one participants over the age of 60 were enrolled through the Knight Alzheimer's Disease Research Center (ADRC) at Washington University School of Medicine (WUSM). Twenty-three patients who were classified as having a Clinical Dementia Rating sum of boxes score of 0 (CDR 0) were determined to be amyloid negative by [$^{11}$C] PIB-PET imaging with mean cortical binding potential (MCBP) score of <0.18 when available and CSF Aβ42 concentration of 1 ng/ml or higher by immunoprecipitation/mass spectrometry (IP/MS) as described elsewhere. See, for example, Patterson et. al, *Annals of Neurology*, 78(3): 439-453. (11 Eighteen patients with a CDR>0 were confirmed to be amyloid positive by [$^{11}$C]PIB-PET (MCBP>0.18) when available and CSF Aβ42 concentration <1 ng/ml by IP/MS.

Participants were admitted to the Clinical Research Unit (CRU) at Washington University at 7:00 AM following an overnight fast. An intravenous (IV) line was placed for serial blood draws. Hour zero (baseline) blood samples were obtained prior to tracer administration. For the IV bolus-labeled studies, the stable isotope tracer was prepared by the clinical pharmacy the morning of the study by dissolving 800 mg of L-[U-13C6] leucine (Cambridge Isotope Laboratories, Inc.) into 150 ml sterile normal saline followed by transfer to an infusion bag through a 0.22 micron filter; it was stored at 4° C. until use. For the oral-labeled studies, the tracer was administered orally by mixing 800 mg of L-[U-13C6] leucine in 300 ml of grape Kool-aid mixed with sucralose sweetener. Participants had 10 minutes to consume the dose followed by a rinse of an additional 100 ml of grade Kool-aid mixed with sucralose sweetener without leucine. Following baseline blood samples, L-[U-13C6] leucine was infused as an IV bolus over 10 minutes. Sixteen of the amyloid negative participants received IV bolus labeling and the remaining 7 received oral labeling. Fifteen of the amyloid positive participants received IV bolus labeling and the remaining three received oral labeling. 20 mL of blood were collected hourly for a total of 20 time points over 24 hours in CARS EDTA tubes (t=0 is the start of labeling). Samples were centrifuged immediately upon collection, and the plasma, buffy coat and red blood cells were stored separately in polypropylene tubes (Axygen) at −80° C. until time of sample processing.

All targeted Aβ isoforms (Aβ38, Aβ40, and Aβ42) were immunoprecipitated simultaneously from 2 mL of plasma via a monoclonal anti-Aβ mid-domain antibody (HJ5.1, anti-Aβ13-28) conjugated to M-270 Epoxy Dynabeads (Life Technologies #14302D) according to manufacturer protocol. Each 1 mL aliquot of plasma was thawed on ice and pre-treated with 20 μL of 100× protease inhibitor (Roche #11140920), 20 μL of 2.5% (w/v) Tween-20 (Sigma #P9416), 50 μL of 10×PBS (Sigma #P3813), and 100 μL of 5M Guanidine (Sigma #G4505). After pre-treatment, 2×1 mL aliquots from each corresponding collection time point were combined and spiked with 20 μL of a solution containing 3.75 pg/μL 12C15N-Aβ38, 25 pg/μL 12C15N-Aβ40, and 2.5 pg/μL $^{12}C^{15}N$-Aβ42 in 4:1 0.1% NH$_4$OH:acetonitrile (ACN). A 50 μL aliquot of antibody-bead slurry containing 15 mg/mL of epoxy-coupled dynabeads (109 beads/mL) was added and the mixtures were rotated at room temperature for 90 minutes. After incubation, the beads were washed twice with 1 mL aliquots of 1×PBS and twice with 1 mL aliquots of 100 mM Triethylammonium bicarbonate (TEABC, Sigma #17902). Washed beads were then aspirated to dryness and treated with 50 μL of neat formic acid (Fisher #A117-50) to elute Aβ species from the antibody-bead complex. The formic acid supernatant was transferred to a new 1.7 mL polypropylene tube and dried in vacuo without heat. The resulting dried precipitate was then treated with 50 μL acetonitrile and dried again in vacuo without heat to remove any residual formic acid. Each sample was then reconstituted in 50 L 100 mM TEABC. Proteolytic digestion was initiated via the addition of a 50 μL aliquot of 2.5 ng/μL LysN metalloprotease (Pierce #90300) in 50 mM TEABC. Digestion was performed overnight (~16 hrs) at 4° C. and 1400 RPM. Digestion reactions were quenched via the addition of a 2 μL aliquot of 50% Trifluoroacetic acid (TFA, Sigma #T6508) and 100 μL of 2% ACN in 0.05% TFA. Quenched digests were loaded onto a C18 TopTip (Glygen #TT2C18.96) previously washed with 60% ACN in 0.05% TFA and equilibrated with 2% ACN in 0.05% TFA. After loading, digests were washed twice with 10% Acetonitrile/0.05% TFA and eluted with 150 μL 60% ACN in 0.05% TFA. Solid phase extraction eluants were then dried in vacuo without heat and stored at −80° C. until analysis.

Extracted digests were reconstituted with 25 μl of 20 nM BSA Digest (Pierce #1863078) in 10% Formic acid/10% acetonitrile. A 4.5 L aliquot of each digest was then subjected to LC-MS/MS on a Thermo Orbitrap Fusion Tribrid mass spectrometer interfaced with a Waters nanoAcquity chromatography system. Reconstituted digests were loaded via direct injection from a 5 μL sample loop onto a Waters 100×0.075 mm Acquity M-class HSS T3 column at 10% ACN in 0.1% formic acid with a flow rate of 600 nL/min for twelve minutes. Peptides were then resolved using a 10 minute linear gradient at 300 nL/min from 10% ACN in 0.1% formic acid to 35% ACN in 0.1% formic acid. The initial gradient was followed by a steeper linear gradient to 90% ACN in 0.1% formic acid over 5 minutes also at 300 nL/min. The column was washed with 90% ACN in 0.1% formic acid for an additional 2 minutes at 600 nL/min prior to re-equilibration to initial conditions for 5 minutes also at 600 nL/min.

In order to determine whether Aβ kinetics in the blood differs between amyloid positive and amyloid negative individuals, SILK time courses were obtained for plasma Aβ38, Aβ40, and Aβ42. Notably, the half-life of the Aβ isoforms in plasma was found to be approximately three hours, considerably faster than previously reported in CSF SILK studies (approximately 9 hours, FIG. 1A). In order to determine plasma Aβ kinetic rates, isotopic enrichment ratios were calculated and plotted versus time to elucidate differences in the kinetics of Aβ isoforms in the blood. For both amyloid negative and amyloid positive individuals, Aβ38 labeling kinetics peaked earlier than Aβ40 and Aβ42, indicating a faster turnover rate. This pattern is unique to plasma Aβ kinetics and was not found in prior CSF Aβ SILK studies.

Figure 1B:
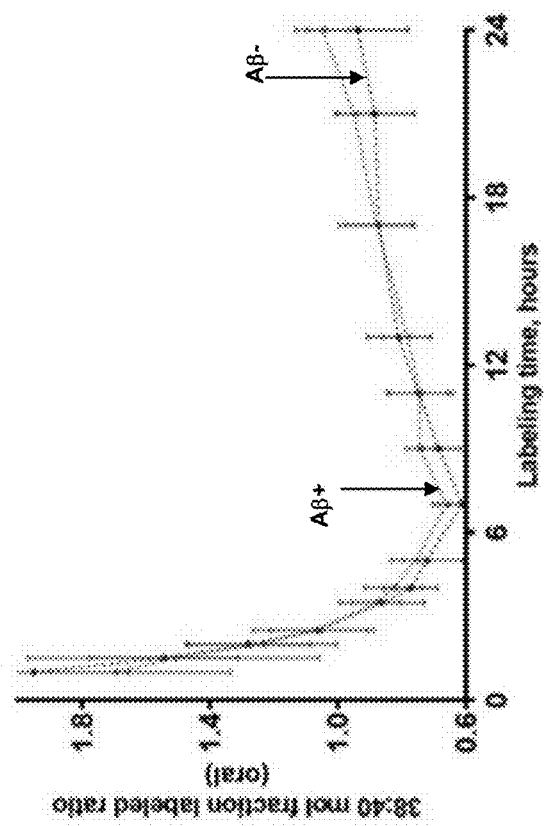
FIG. 1B shows the average isotopic enrichment ratios for plasma Aβ38/Aβ40 displaying both amyloid groups on the same plot (blue, amyloid negative; red, amyloid positive) (mean+/−95% CI) demonstrates similar rates of plasma Aβ38/Aβ40 turnover regardless of amyloid status or labeling protocol (left, IV bolus; right, oral).
Figure 1B:
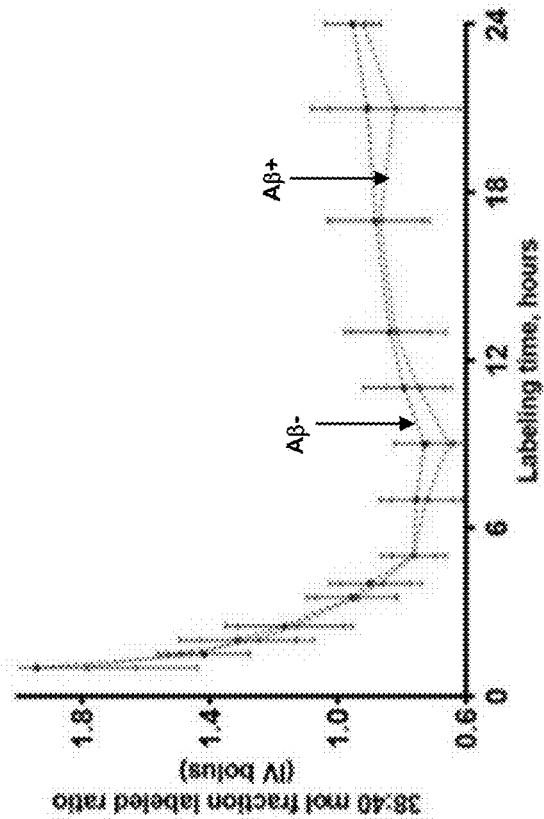
Figure 1C:
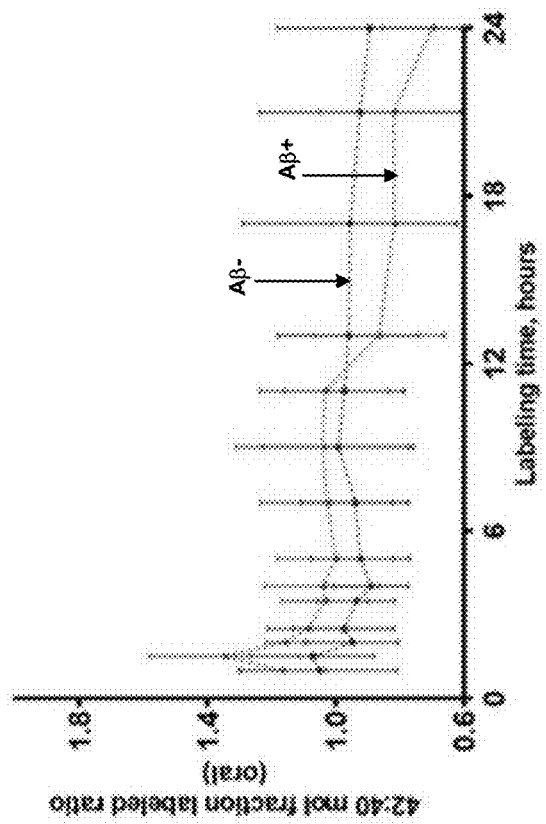
FIG. 1C shows the average isotopic enrichment ratios for plasma Aβ42/Aβ40 displaying both amyloid groups on the same plot (blue, amyloid negative; red, amyloid positive) highlights the faster Aβ42 turnover kinetics in the amyloid positive group (mean+/−95% CI) for both the IV-bolus (left) and oral-labeled groups (right).
Figure 1C:
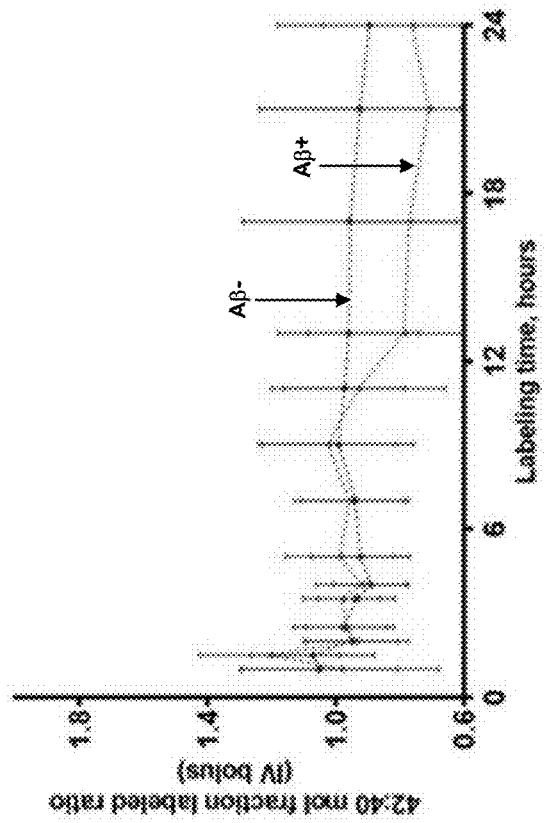

In prior CSF studies, Aβ42 peaked earlier than Aβ38 and Aβ40 in amyloid positive individuals (3) indicating a faster loss of soluble Aβ42 due to aggregation. In this plasma SILK study, the Aβ38/Aβ40 ratios were similar over time between amyloid groups (FIG. 1B), indicating no difference in kinetic processing between Aβ38 and Aβ40. In contrast, the plasma SILK Aβ42/Aβ40 ratios demonstrated faster soluble Aβ42 turnover kinetics in amyloid positive individuals (FIGS. 1B, 1C), as seen in prior reports of Aβ CSF SILK (2,3). While the average SILK Aβ42/Aβ40 ratio remained close to unity in the amyloid negative group, a drop after hour 12 in the Aβ42/Aβ40 ratio of the amyloid positive group indicates faster Aβ42 turnover and aggregation in those with CNS amyloidosis (FIG. 1C).

Figure 2A:
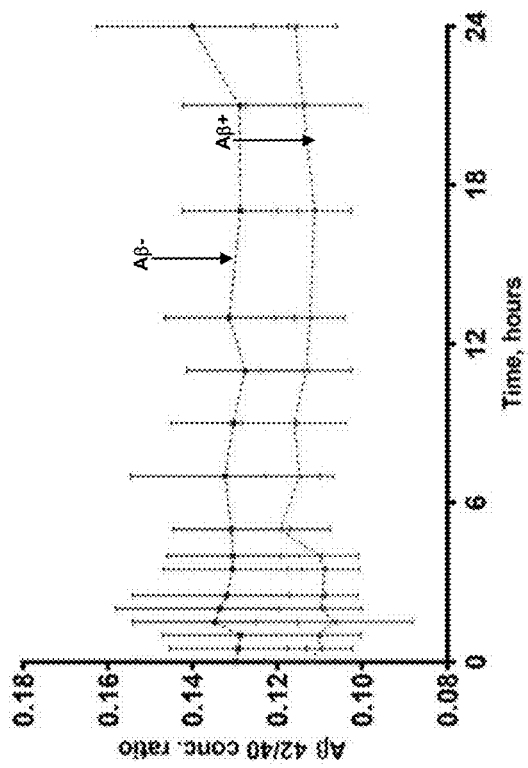
FIG. 2A depicts the concentration of Aβ42/Aβ40 over time averaged by clinical group (blue, amyloid negative; red, amyloid positive) (mean+/−95% CI). Both Aβ42/Aβ40 and Aβ42 concentrations were 10-15% lower in the amyloid positive group compared to the amyloid negative group at all time points measured.
Figure 2B:
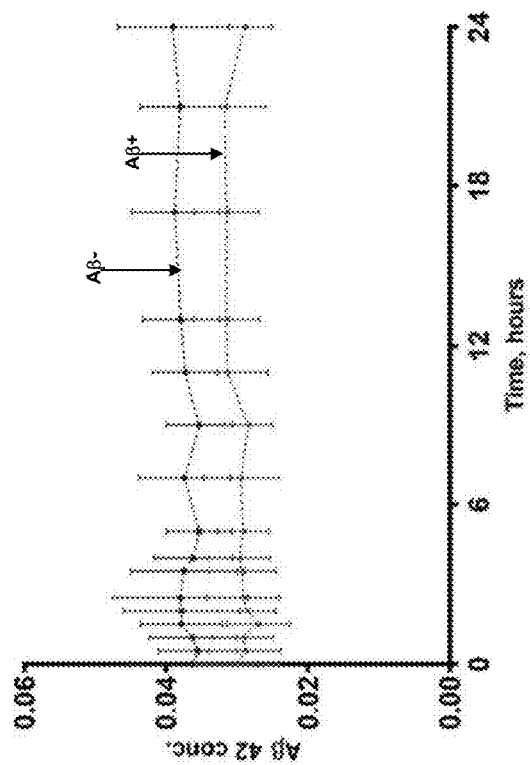
FIG. 2B shows the concentrations of Aβ42 over time averaged by clinical group (blue, amyloid negative; red, amyloid positive) (mean+/−95% CI).
Figure 2C:
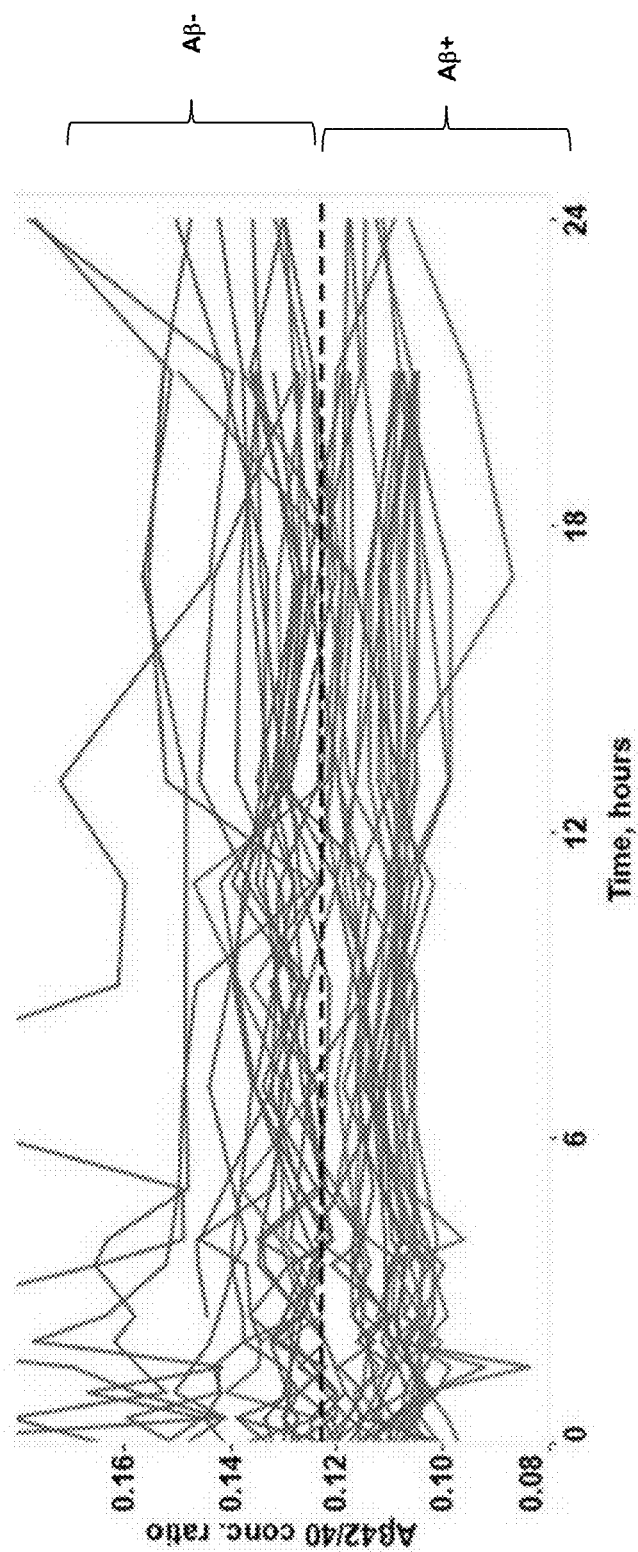
FIG. 2C shows the concentrations of Aβ42/Aβ40 over time with individual participant time courses illustrates the consistency of concentration measurements (blue, amyloid negative; red, amyloid positive).
Figure 3A:
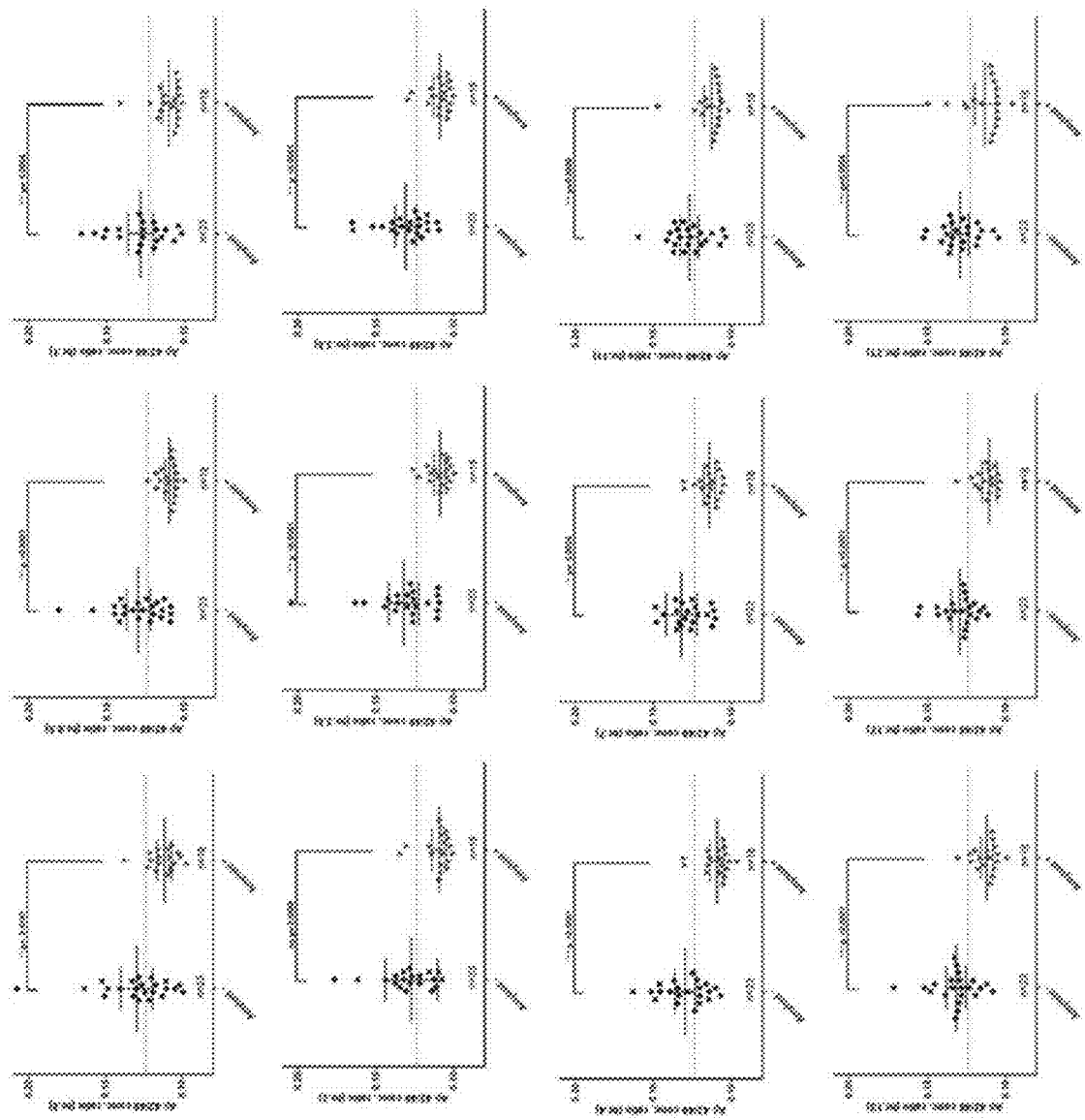
FIG. 3A shows the average Aβ42/Aβ40 concentrations at all time points separated by amyloid status (with amyloid negative blue and amyloid positive red).
Figure 3B:
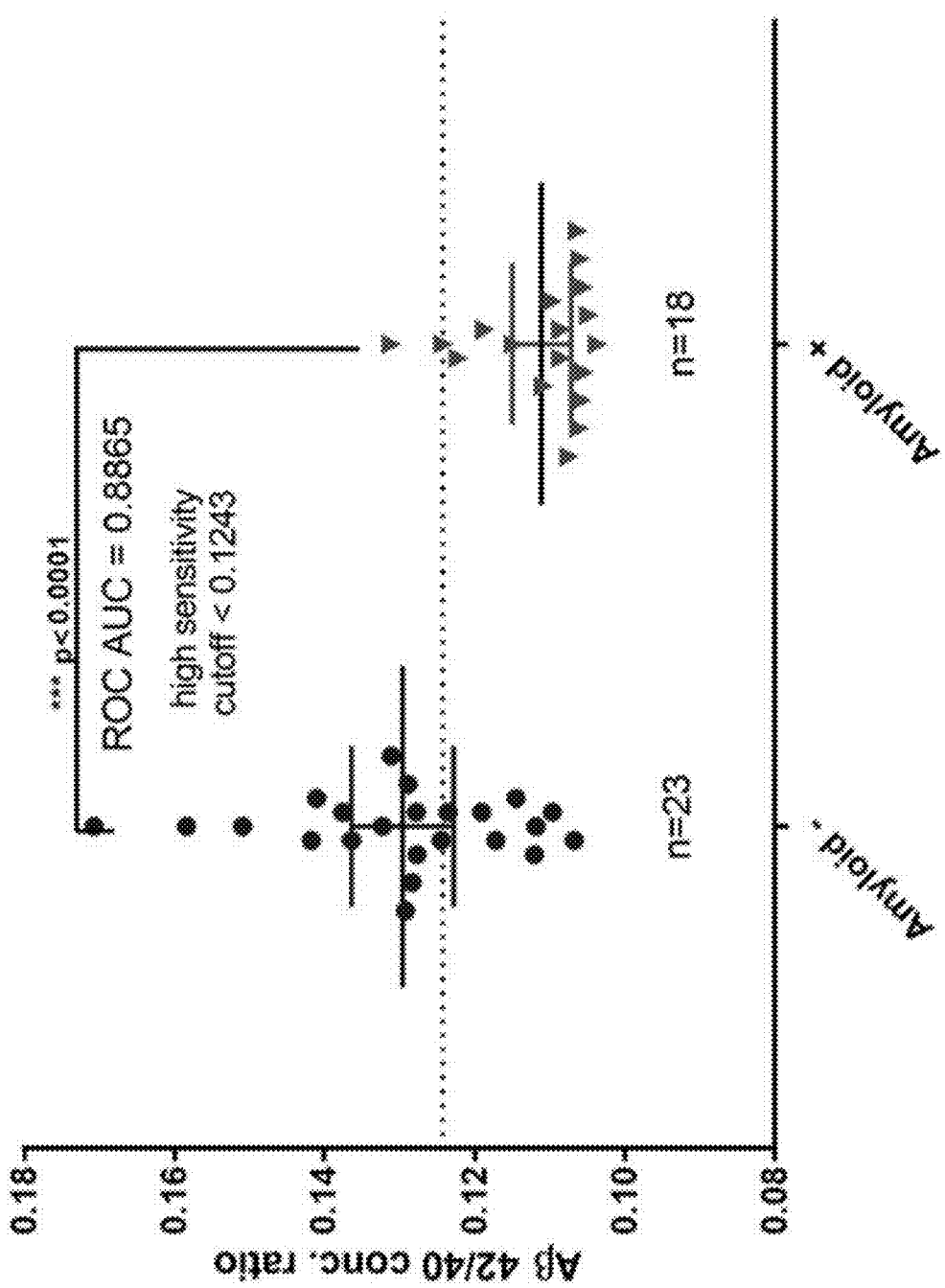
FIG. 3B shows Aβ42/Aβ40 concentrations by amyloid status as an average of all time points (0-24 hours). On average, the Aβ42/Aβ40 concentration was 0.1297+/−0.0033 in the amyloid negative group (blue) and 0.1111+/−0.0019 in the amyloid positive group (red). This reflects a 14.3% lower Aβ42/Aβ40 concentration in amyloid positive individuals compared to amyloid negative individuals overall. (p value<0.0001, mean+/−95% CI shown).

Human plasma samples were also analyzed for concentrations of Aβ38, Aβ40, and Aβ42 at each time point to investigate the production rates and whether CNS amyloidosis is associated with plasma Aβ differences. The Aβ42 concentrations and Aβ42/Aβ40 concentration ratios were significantly lower in the amyloid positive cohort compared to the amyloid negative cohort, and this finding was consistent in longitudinal samples over 24 hours (FIG. 2). Average Aβ42/Aβ40 throughout the study demonstrated similar values within the amyloid negative group. While Aβ42/Aβ40 differences were small between amyloid groups, they were statistically significant at most time points measured throughout the study (FIG. 3A). An average of Aβ concentrations over the time period demonstrates excellent precision for identifying CNS amyloidosis (FIG. 3B). Regarding the diagnostic accuracy of amyloidosis, CNS amyloidosis with plasma normal results were rare, while CNS non-amyloidosis with plasma positive was more common. A similar pattern of decreased Aβ42/Aβ40 ratios in the presence of amyloidosis is observed in CSF, which is hypothesized to be due to Aβ42 concentrations decreasing before detection of accumulation by amyloid PET.

The magnitude of the difference in plasma is less than detected in CSF. While Aβ42/Aβ40 ratios in the CSF are decreased by approximately 50% in the presence of amyloidosis, in plasma Aβ42/Aβ40 ratios are decreased by 14.3% on average in amyloid positive relative to amyloid negative individuals (FIG. 3B). Despite these relatively small differences in Aβ42/Aβ40 concentration ratios between amyloid pathology groups, they were quantified by high resolution mass spectrometry with good stability over time suggesting reliability of this measurement as a biomarker for amyloidosis.

Figure 4:
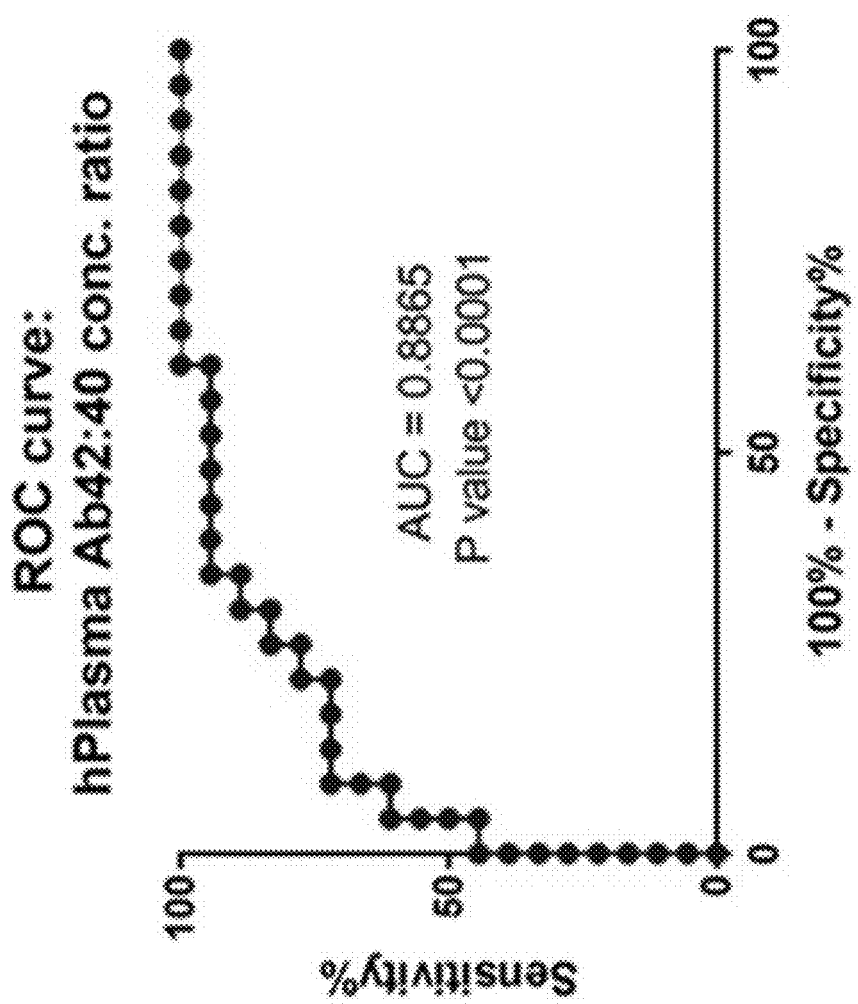
FIG. 4 depicts a ROC curve analysis using average plasma Aβ42/Aβ40 concentration ratios over 24 hours that were measured as described in Example 1. The ROC curve has an AUC of 0.8865, indicating good accuracy as a diagnostic test to detect Aβ amyloidosis. Accordingly, a skilled artisan may use the ROC curve to select a threshold value where sensitivity and specificity both have acceptable values for a given clinical situation, and this value can be used in applying the test for diagnostic or treatment purposes.
Figure 5:
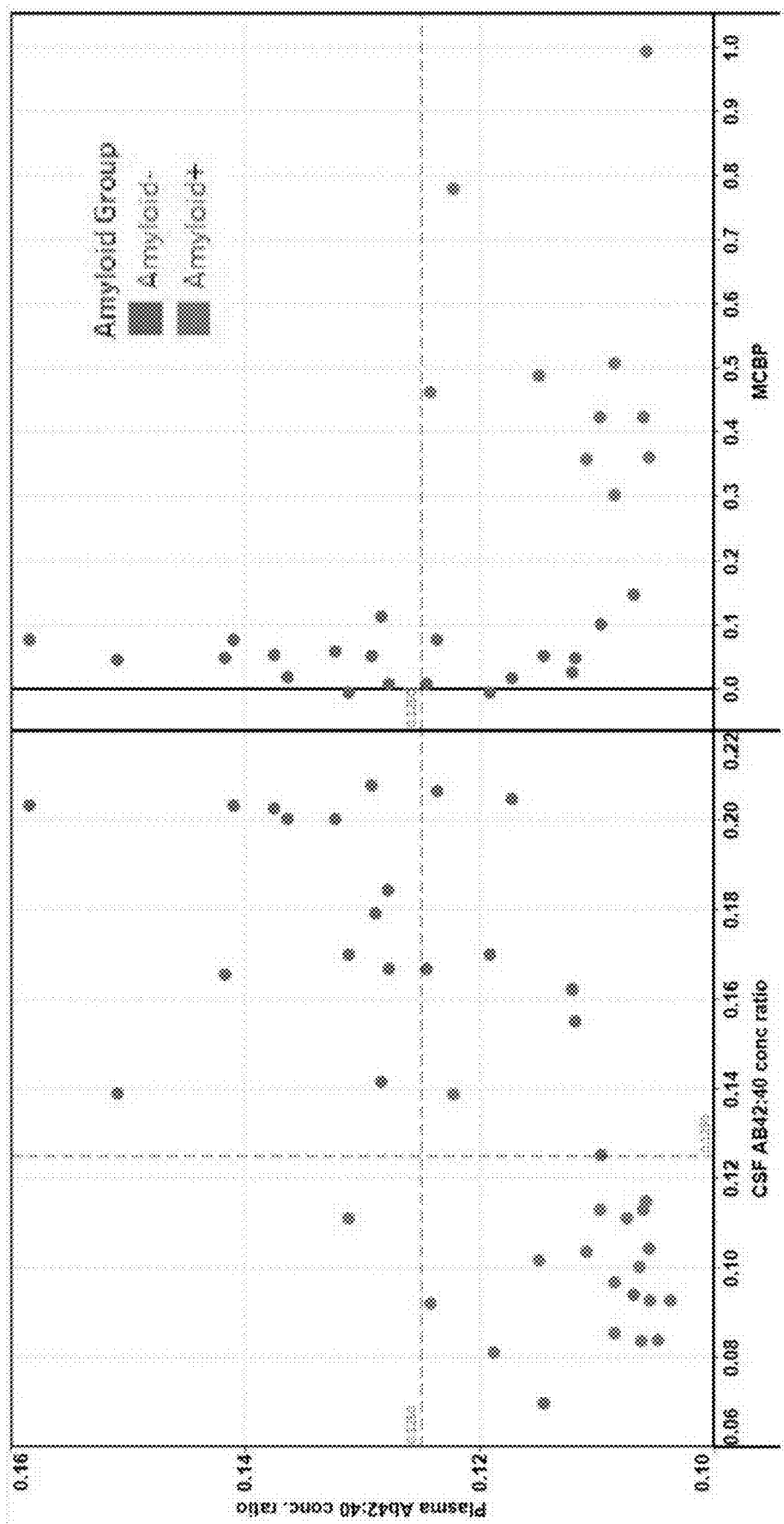
FIG. 5 depicts a graph showing the concentration of plasma Aβ42/Aβ40 as compared to CSF Aβ42/Aβ40 and MCBP. Amyloid positive subjects are indicated in blue and amyloid negative subjects are indicated in red. Experimental details regarding the subjects and measurement of CSF Aβ42/Aβ40 and MCBP can be found in the Example.
Figure 6:
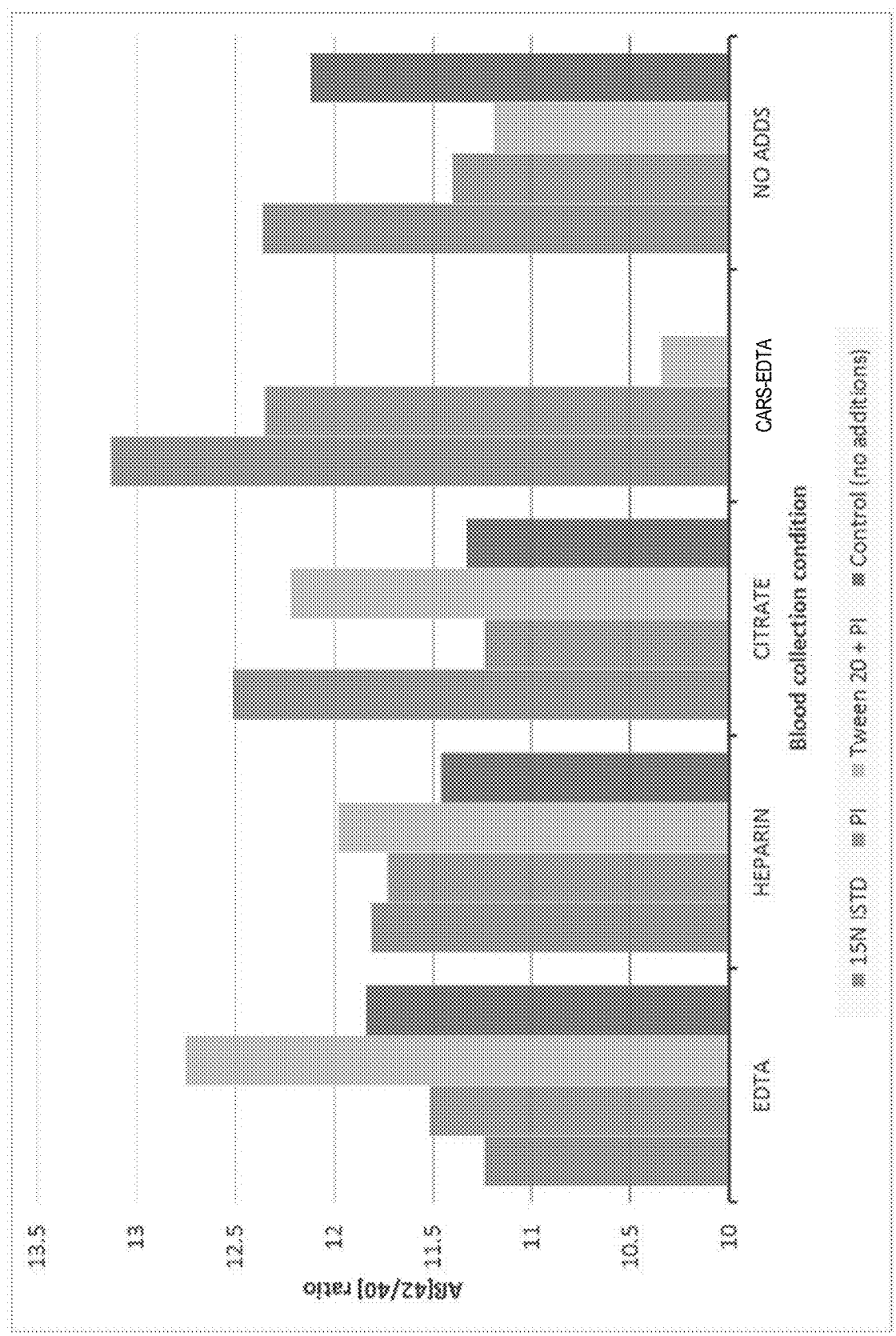
FIG. 6 depicts graphs showing the effect of various plasma treatment conditions on the Aβ42/Aβ40 ratio. "CARS-EDTA" is a type of clinical EDTA tube used for blood collection.
Figure 7A:
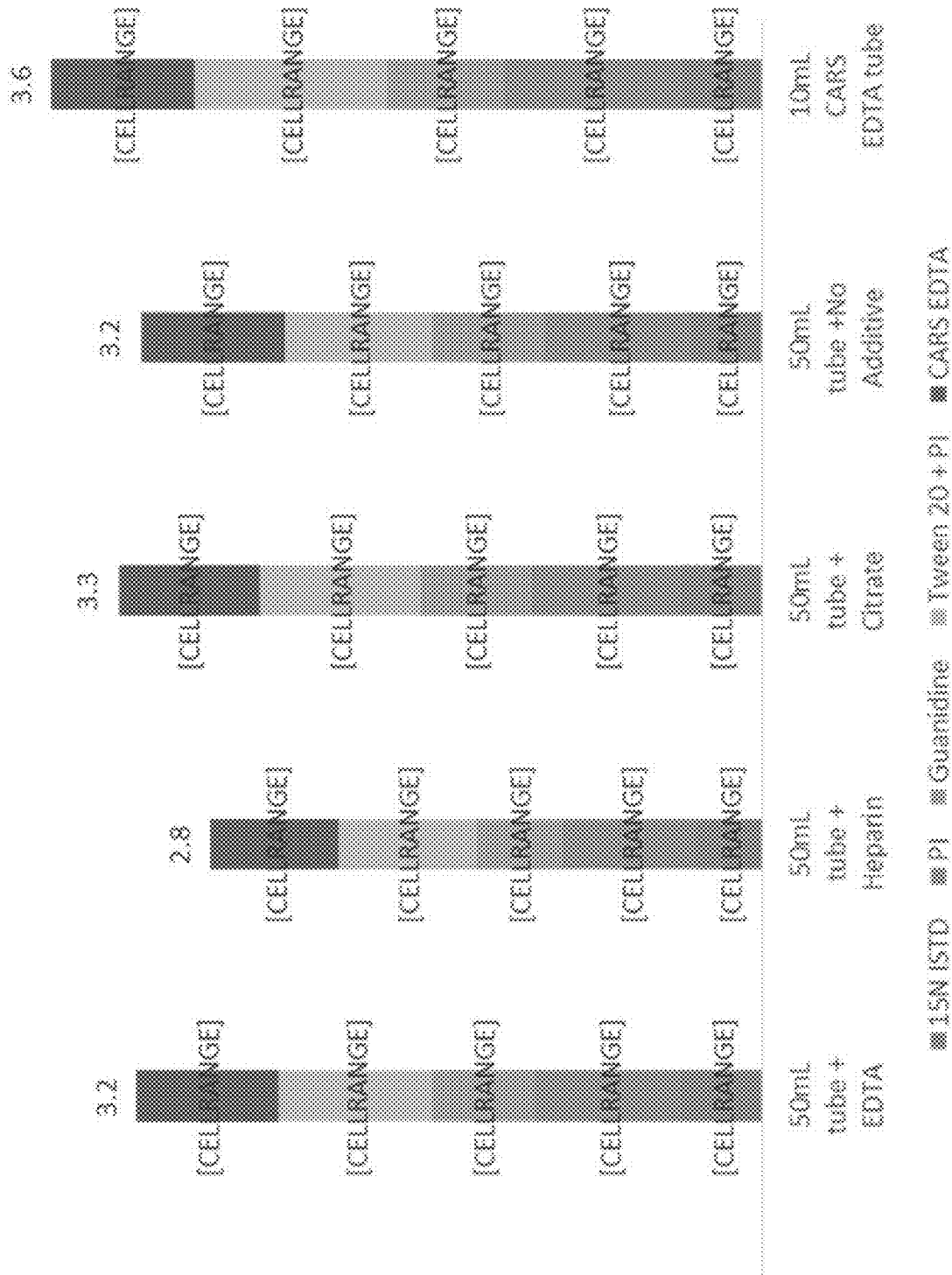
FIG. 7 depicts stack column charts of the relative Aβ40 (left) and Aβ42 (right) recovery following sample processing as described in Example 3. Both Aβ40 and Aβ42 have the highest recovery (highest columns) from 10 mL pink top CARS EDTA (far right) among the tubes used, with 3.6 a.u. and 4.4 a.u., respectively. Percent yield of both Aβ40 and Aβ42 using additives (colored) were not significantly better than CARS tube with no additives (blue color on top of each column).
Figure 7B:
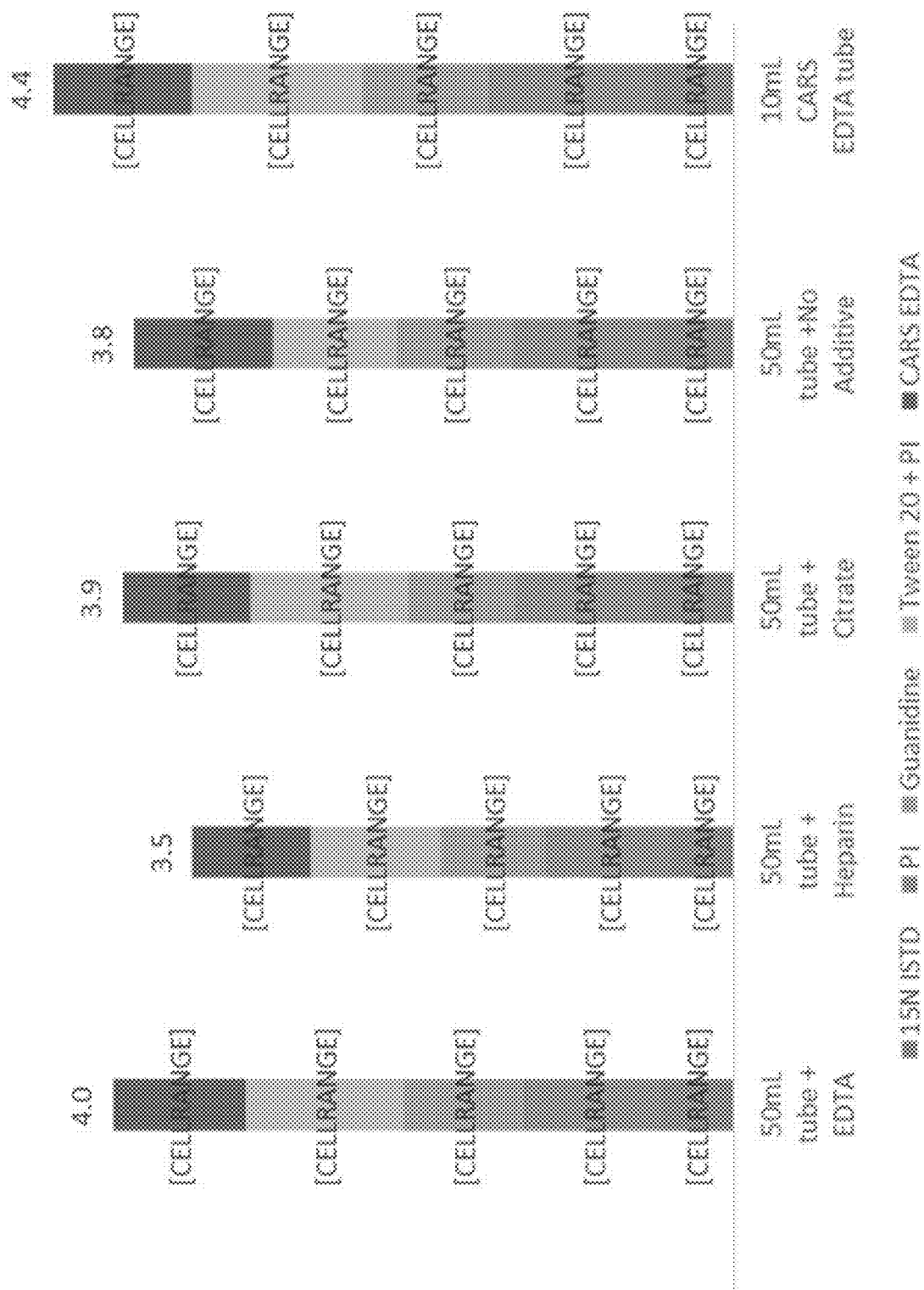

To investigate the utility of measuring absolute plasma Aβ concentrations as a biomarker for amyloidosis, a receiver operating characteristic (ROC) curve was generated from the averaged plasma Aβ42/Aβ40 concentration ratios. This ROC analysis demonstrates an area under the curve (AUC) of 0.8865. As a combined measure of sensitivity and specificity, the AUC describes the inherent validity of using this plasma biomarker as a metric for predicting amyloid status. An AUC of 0.8865 indicates the absolute Aβ42/Aβ40 concentration ratio from human plasma has good diagnostic accuracy for the detection of amyloidosis. In other words, there is an 89% probability that a randomly chosen individual with amyloidosis would have a lower plasma Aβ42/Aβ40 concentration ratio compared to a randomly chosen individual without amyloidosis. Furthermore, using the Youden index to determine optimal cutoff values, a threshold of 0.1243 maximizes sensitivity and specificity of the plasma Aβ42/Aβ40 concentration ratio as a tool for amyloid status classification. (FIG. 4).

Example 2

A standard protocol for blood collection is in 10 mL pink top CARS EDTA tubes. Plasma separates from red cell when spun down, collected, aliquoted into 1 mL Axygen tubes, and stored at −80 C until use. There was the uncertainty whether or not the blood collection procedure was optimal for the maximum recovery of the Aβ. Therefore, an experiment was designed to determine which of EDTA, Heparin and Citrate containing tubes would be ideal for blood collection for stable Aβ measurements. In addition, several additives were tested at the blood collection step in these various tubes, with the CARS EDTA tubes in the standard protocol used as a control, for each tube and additive being tested. Data from all these experimental conditions were compared to the standard protocol of blood collection in CARS EDTA tube with no additives during blood collection. In addition, freeze/thaw impact on Aβ measurements was tested for each condition and compared to plasma processed and analyzed fresh. Aβ was analyzed by LC/MS on Orbitrap Fusion Lumos mass spectrometer.

Human subjects were administered 400 mg C13-leucine as an IV bolus. Three hours post-administration, 250 ml of total blood was collected. 50 ml aliquots were distributed into 50 ml conical tubes that were untreated or pretreated with EDTA (1.8 mg per ml of blood), Heparin (15.8 USP units per ml of blood), Citrate (0.218M), in addition to the Standard Control protocol collected in 10 mL pink top CARS EDTA tubes. These 50 mL tubes were split into 10 mL collection tubes with the following additives added: uniformly labeled N15 internal standards Aβ, protease inhibitor (2× Roche Complete Protease Inhibitor cocktail), 0.5 M Guanidine, 0.05% Tween-20 and protease inhibitor (2×) combination. The 10 mL pink top CARS EDTA tubes with no additives were used as controls. These 10 mL tubes were then spun down to produce 5 mLs plasma and then split into 2.5 mLs aliquots. One set from each condition were flash frozen in dry ice and the others 2.5 mLs aliquots were left unfrozen. All samples were brought back to the lab for immediate processing by the IP/MS protocol described in Example 1. See also, Ovod et al., *Alzheimer's & Dementia*, 13(2017): 841-849. The only exception was that any additives that were already added to the plasma in the clinic were not added again during sample processing.

The data from these experiments are shown in Tables 1-4. One main observation made during sample processing was that guanidine containing samples showed signs of hemolysis, therefore, affecting the integrity of the plasma Aβ. Analysis of these guanidine treated blood samples showed lower Aβ recovery compared to control CARS tube with no additives. The only additive condition showing higher Aβ recoveries were adding protease inhibitor and tween-20 combination to the CARS tubes before blood collection. There were about 10 to 20% more Aβ40 and Aβ42 recovery. Adding protease inhibitor alone produces the same effects. However, regardless of the additives, the Aβ[42/40] ratios remain the same and more stable for the current protocol collecting blood in 10 mL pink top CARS tube without any additives. Therefore, there was no net benefit of having additives in the tubes prior to plasma collection. Plasma Aβ40 analyzed from CARS Heparin tubes were about 10% lower compared to CARS EDTA tubes, whereas citrate made no difference. Aβ42 analyzed from CARS Heparin tubes were about 15% and citrate tubes about 10% lower than analyzed from CARS EDTA tubes. More importantly, Aβ[42/40] ratios measured were more stable in CARS EDTA tubes, even with a freeze-thaw of the plasma samples. Freeze-thaw had no distinctive effect on plasma Aβ42 and Aβ40 measured, resulting in very reproducible Aβ[42/40] ratios from CARS EDTA tubes. In conclusion, none of the tubes and additives tested performed better than the 10 mL pink top CARS EDTA tubes used for blood collection.

TABLE 1

Percent Aβ38 gain

| Treatment | 15N ISTD | PI | Guanidine | Tween 20 + PI | No Additives |
|---|---|---|---|---|---|
| EDTA Frozen | 93 | 107 | 45 | 227 | 148 |
| Heparin Frozen | 42 | 89 | 58 | 151 | 119 |
| Citrate Frozen | 73 | 73 | 37 | 236 | 115 |
| CARS Frozen | 100 | 100 | 100 | 100 | 100 |
| No Adds Frozen | 112 | 79 | 48 | 211 | — |

TABLE 2

Percent Aβ40 gain

| Treatment | 15N ISTD | PI | Guanidine | Tween 20 + PI | No Additives |
|---|---|---|---|---|---|
| EDTA Frozen | 85 | 107 | 47 | 156 | 174 |
| Heparin Frozen | 50 | 99 | 52 | 162 | 144 |
| Citrate Frozen | 65 | 79 | 53 | 170 | 150 |
| CARS Frozen | 100 | 100 | 100 | 100 | 100 |
| No Adds Frozen | 102 | 80 | 43 | 166 | — |

TABLE 3

Percent Aβ42 gain

| Treatment | 15N ISTD | PI | Guanidine | Tween 20 + PI | No Additives |
|---|---|---|---|---|---|
| EDTA Frozen | 67 | 96 | 55 | 127 | 135 |
| Heparin Frozen | 35 | 98 | 53 | 137 | 139 |
| Citrate Frozen | 63 | 88 | 69 | 158 | 169 |
| CARS Frozen | 100 | 100 | 100 | 100 | — |
| No Adds Frozen | 96 | 74 | 74 | 108 | 100 |

TABLE 4

Aβ42/Aβ40 ratio

| Treatment | 15N ISTD | PI | Guanidine | Tween 20 + PI | No Additives |
|---|---|---|---|---|---|
| EDTA Frozen | 11.24 | 11.52 | 14.62 | 12.75 | 11.84 |
| Heparin Frozen | 11.81 | 11.73 | 14.73 | 11.98 | 11.46 |
| Citrate Frozen | 12.51 | 11.24 | 12.12 | 12.22 | 11.33 |
| CARS Frozen | 13.13 | 12.35 | 12.95 | 10.34 | — |
| No Adds Frozen | 12.36 | 11.40 | 13.68 | 11.19 | 12.12 |

REFERENCES

1. Selkoe D J, Hardy J. The amyloid hypothesis of Alzheimer's disease at 25 years. EMBO Mol Med. 2016; 8(6): 595-608.
2. Potter R, Patterson B W, Elbert D L, Ovod V, Kasten T, Sigurdson W, Mawuenyega K, Blazey T, Goate A, Chott R, Yarasheski K E, Holtzman D M, Morris J C, Benzinger T L, Bateman R J. Increased in vivo amyloid-r342 production, exchange, and loss in presenilin mutation carriers. Sci Transl Med. 2013; 5(189)
3. Patterson B W, Elbert D L, Mawuenyega K G, Kasten T, Ovod V, Ma S, Xiong C, Chott R, Yarasheski K, Sigurdson W, Zhang L, Goate A, Benzinger T, Morris J C, Holtzman D, Bateman R J. Age and amyloid effects on human CNS amyloid-beta kinetics. Ann Neurol. 2015; 78(3): 439-453.
4. Beach T G, Monsell S E, Phillips L E, Kukull W. Accuracy of the clinical diagnosis of Alzheimer disease at National Institute on Aging Alzheimer's disease Centers, 2005-2010. J Neuropathol Exp Neurol. 2013; 71(4): 266-273.
5. Cohen A D, Klunk W E. Early detection of Alzheimer's disease using PiB and FDG PET. Neurobiol Dis. 2014; 72 Pt A:117-22.
6. Galasko D, Chang L, Motter R, Clark C M, Kaye J, Knopman D, Thomas R, Kholodenko D, Schenk D, Lieberburg I, Miller B, Green R, Basherad R, Kertiles L, Boss M A, Seubert P. High cerebrospinal fluid tau and low amyloid beta42 levels in the clinical diagnosis of Alzheimer disease and relation to apolipoprotein E genotype. Arch Neurol. 1998; 55(7):937-45.
7. Clark C M, Xie S, Chittams J, Ewbank D, Peskind E, Galasko D, Morris J C, McKeel D W, Jr., Farlow M, Weitlauf S L, Quinn J, Kaye J, Knopman D, Arai H, Doody R S, DeCarli C, Leight S, Lee V M, Trojanowski J Q. Cerebrospinal fluid tau and beta-amyloid: how well do these biomarkers reflect autopsy-confirmed dementia diagnoses? Arch Neurol. 2003; 60(12):1696-702.
8. Mayeux R, Honig L S, Tang M X, Manly J, Stern Y, Schupf N, Mehta P D. Plasma A[beta]40 and A[beta]42 and Alzheimer's disease: relation to age, mortality, and risk. Neurology. 2003; 61(9): 1185-90.
9. Yaffe K, Weston A, Graff-Radford N R, Satterfield S, Simonsick E M, Younkin S G, Younkin L H, Kuller L, Ayonayon H N, Ding J, Harris T B. Association of plasma beta-amyloid level and cognitive reserve with subsequent cognitive decline. JAMA. 2011; 305(3):261-6.
10. Bateman R J, Munsell L Y, Morris J C, Swarm R, Yarasheski K E, Holtzman D M. Human amyloid-B synthesis and clearance rates as measured in cerebrospinal fluid in vivo. Nat Med. 2006; 12(7): 856-861.
11. Mawuenyega K G, Kasten T, Sigurdson W, Bateman R J. Amyloid-beta isoform metabolism quantitation by stable isotope-labeled kinetics. Anal Biochem. 2013; 440 (1): 56-62.
12. Roberts K F, Elbert D L, Kasten T P, Patterson B W, Sigurdson W C, Connors R E, Ovod V, Munsell L Y, Mawuenyega K G, Miller-Thomas M M, Moran C J, Cross, DT III, Derdeyn C P, Bateman R J. Amyloid-B efflux from the CNS into the plasma. Ann Neurol. 2014; 76(6): 837-844.
13. Deane R, Du Yan S, Submamaryan R K, LaRueB, Jovanovic S, Hogg E, Welch D, Manness L, Lin C, Yu J, Zhu H, Ghiso J, Grangione B, Stern A, Schmidt A M, Armstrong D L, Arnold B, Liliensiek B, Nawroth P, Hofman F, Kindy M, Stern D, Zlokovic B. RAGE mediates amyloid-beta peptide transport across the blood-brain barrier and accumulation in brain. Nat Med. 2003; 9(7): 907-913.
14. Dean R, Wu Z, Sagare A, Davis J, Du Yan S, Hamm K, Xu F, Parisi M, LaRue B, Hu H W, Spijkers P, Guo H, Song X, Lenting P J, Van Nostrand W E, Zlokovic B V. LRP/amyloid beta-peptide interaction mediates differential brain efflux of Abeta isoforms. Neuron. 2004; 5(3): 333-44.
15. Fukumoto H, Tennis M, Locascio J J, Hyman B T, Grwodon J H, Irizarry M C. Age but not diagnosis is the main predictor of plasma amyloid beta-protein levels. Arch Neurol. 2003; 60:958-964.
16. T. Sobów, M. Flirski, I. Ktoszewska, P. P. Liberski. Plasma levels of alpha beta peptides are altered in amnestic mild cognitive impairment but not in sporadic Alzheimer's disease. Acta. Neurobiol. Exp. (Wars), 65 (2005), pp. 117-124.
17. Mayeux R, Schupf N. Blood-based biomarkers for Alzheimer's disease: plasma Ab40 and Aβ42, and genetic variants. Neurobio of Aging. 2011; 32(11): S10-S19.

What is claimed is:

1. A method for detecting Aβ amyloidosis in a subject, the method comprising:
   (a) measuring the concentration of Aβ42 and Aβ40 in a blood sample obtained from the subject, and then calculating the Aβ42/Aβ40 value, where the measuring comprises contacting the blood sample with an anti-Aβ antibody preparation that is substantially free of Aβ contamination, wherein the anti-Aβ antibody preparation is produced in serum-free medium;
   (b) comparing the calculated Aβ42/Aβ40 value to a threshold Aβ42/Aβ40 value of about 0.126, wherein an Aβ42/Aβ40 value less than the threshold Aβ42/Aβ40 value indicates Aβ amyloidosis;
   (c) administering one or more of cholinesterase inhibitor, N-methyl D-aspartate antagonist, antidepressant, gamma-secretase inhibitor, beta-secretase inhibitor, anti-Aβ antibody, stem cell therapy, dietary supplement, serotonin receptor 6 antagonist, p38alpha MAPK inhibitor, recombinant granulocyte macrophage colony-stimulation factor, passive immunotherapy, active vaccine, tau protein aggregation inhibitor, anti-inflammatory agent, phosphodiesterase 9A inhibitor, sigma-1 receptor agonist, kinase inhibitor, angiotensin receptor blocker, CB1 and/or CB2 endocannabinoid receptor partial agonist, β-2 adrenergic receptor agonist, nicotinic acetylcholine receptor agonist, 5-HT2A inverse agonist, alpha-2c adrenergic receptor antagonist, 5-HT 1A and 1D receptor agonist, Glutaminyl-peptide cyclotransferase inhibitor, selective inhibitors of APP production, monoamine oxidase B inhibitor, glutamate receptor antagonist, AMPA receptor agonist, nerve growth factor stimulant, HMG-COA reductase inhibitor, neurotrophic agent, muscarinic M1 receptor agonist, GABA receptor modulator, PPAR-gamma agonist, microtubule protein modulator, calcium channel blocker, antihypertensive agent, and statins to the subject with detected Aβ amyloidosis as determined by step (b).

2. The method of claim 1, wherein the calculated Aβ42/Aβ40 value is about 0.125 or less.

3. The method of claim 1, wherein the threshold Aβ42/Aβ40 value is about 0.09.

4. The method of claim 1, wherein the threshold Aβ42/Aβ40 value is calculated using a receiver operating characteristic (ROC) area under the curve (AUC).

5. The method claim 1, wherein the subject was not previously diagnosed with Aβ amyloidosis and/or is asymptomatic.

6. The method of claim 1, wherein the method further comprises administering a further diagnostic test for Aβ amyloidosis, or diseases associated with Aβ amyloidosis selected from measuring the concentration of one or more biomolecules selected from one or more of tau, phospho-tau, and ApoE; structural imaging tests; functional imaging tests; and/or molecular imaging tests.

7. The method of claim 1, further comprising measuring the concentration of another Aβ variant (Aβxx) in the blood sample.

8. The method of claim 7, wherein Aβxx is Aβ38.

* * * * *